(12) United States Patent
Oh et al.

(10) Patent No.: US 9,593,321 B2
(45) Date of Patent: Mar. 14, 2017

(54) L-ARABINOSE ISOMERASE VARIANTS WITH IMPROVED CONVERSION ACTIVITY AND METHOD FOR PRODUCTION OF D-TAGATOSE USING THEM

(71) Applicant: CJ Cheiljedang Corporation, Seoul (KR)

(72) Inventors: In Seok Oh, Incheon (KR); Chang Gyeom Kim, Seoul (KR); Seung Hyun Cho, Seoul (KR); Seong Bo Kim, Gyeonggi-do (KR); Yang Hee Kim, Gyeonggi-do (KR); Kyong Yeon Cho, Seoul (KR); Sung Jae Yang, Gyeonggi-do (KR); Jin Ha Kim, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 15/112,232

(22) PCT Filed: Apr. 25, 2014

(86) PCT No.: PCT/KR2014/003658
§ 371 (c)(1),
(2) Date: Jul. 18, 2016

(87) PCT Pub. No.: WO2015/133678
PCT Pub. Date: Sep. 11, 2015

(65) Prior Publication Data
US 2016/0333335 A1    Nov. 17, 2016

Related U.S. Application Data

(63) Continuation of application No. PCT/KR2014/001789, filed on Mar. 5, 2014.

(51) Int. Cl.
*C12N 9/90* (2006.01)
*C12N 1/20* (2006.01)
(Continued)

(52) U.S. Cl.
CPC .............. *C12N 9/90* (2013.01); *C12N 1/20* (2013.01); *C12N 15/77* (2013.01); *C12P 19/02* (2013.01);
(Continued)

(58) Field of Classification Search
None
See application file for complete search history.

(56) References Cited

U.S. PATENT DOCUMENTS

2003/0022844 A1* 1/2003 Bertelsen ................. C12N 9/90
514/23
2003/0129710 A1* 7/2003 Hansen .................... C12N 9/90
435/105

(Continued)

FOREIGN PATENT DOCUMENTS

BE  WO 2013150069 A1 * 10/2013 ..... C12Y 503/01004
KR  10-2010-0016948 A    2/2010
(Continued)

OTHER PUBLICATIONS

Books in Brief: Ausubel et al., Editors, Current Protocols in Molecular Biology, John Wiley & Sons, Inc., New York 1987, TIBS 13, Aug. 1988, p. 324.
(Continued)

*Primary Examiner* — Robert Mondesi
*Assistant Examiner* — Richard Ekstrom
(74) *Attorney, Agent, or Firm* — Swanson & Bratschun, L.L.C.

(57) ABSTRACT

The present invention relates to the development of an L-arabinose isomerase variant from *Thermotoga neapoli-*
(Continued)

*tana* DSM 5068, which is a kind of thermophile, on the basis of protein molecular modeling. Moreover, the present invention relates to a method of producing D-tagatose from D-galactose by using the enzyme or a microorganism of the genus *Corynebacterium* expressing the enzyme.

16 Claims, 7 Drawing Sheets

(51) Int. Cl.
   *C12P 19/02* (2006.01)
   *C12P 19/24* (2006.01)
   *C12N 15/77* (2006.01)
(52) U.S. Cl.
   CPC ....... *C12P 19/24* (2013.01); *C12Y 503/01004* (2013.01)

(56) References Cited

U.S. PATENT DOCUMENTS

| | | | | |
|---|---|---|---|---|
| 2003/0175909 A1* | 9/2003 | Kim | ........................ | C12N 9/90 435/94 |
| 2004/0058419 A1* | 3/2004 | Pyun | ........................ | C12N 9/90 435/101 |
| 2010/0173366 A1* | 7/2010 | Rhimi | ...................... | C12N 9/90 435/94 |

FOREIGN PATENT DOCUMENTS

| | | | | |
|---|---|---|---|---|
| TN | WO 2009066127 A1 * | 5/2009 | ........... | A23C 9/1206 |
| WO | WO 2004-007738 A | 1/2004 | | |

OTHER PUBLICATIONS

Dische and Borenfreund., A New Spectrophotometric Method for the Detection and Determination of Keto Sugars and Trioses, J. Biol. Chem., 1951, 192:583-587.
Dube and Loeb, Mutants generated by the insertion of random oligonucleotides into the active-site of the beta-lactamase gene, Biochemistry Jul. 1989, 28(14):5703-5707.
Eigen and Gardiner, Evolutionary molecular engineering based on RNA replication, Pure & Appl. Chem. 1984, 56(8):967-978.
Horwitz and Loeb, Promoters selected from random DNA-sequences, Proc. Natl. Acad. Sci. USA, Oct. 1986, 83:7405-7409.
International Search Report issued in PCT/KR2015/003658 on Dec. 5, 2014.
Manjasetty and Chance, Crystal structure of *Escherichia coli* L-arabinose isomerase (ECAI), the putative target of biological tagatose production, J. Mol. Biol., 2006. 360:297-309.
Mulholland, Modeling enzyme reaction mechanisms, specificity and catalysis, Drug Discov. Today. Oct. 2005. 10(20):1393-1402.
Noh et al., Effects of cloned genes on the stability of shuttle vectors between *Escherichia coli* and *Corynebacterium glutamicum*, Kor. Jour. Microbiol. Jul. 1991, 29(3):149-154.
Oh, et al., Increase in D-tagatose production rate by site-directed mutagenesis of L-arabinose isomerase from *Geobacillus thermodenitrificans*, Biotechnology Letters, Feb. 2006, 28(3):145-149.
Rhimi et al., Probing the essential catalytic residues and substrate affinity in the thermoactive *Bacillus stearothermophilus* US100 L-arabinose isomerase by site-directed mutagenesis. Journal of Bacteriology, May 2007, 189(9):3556-3563.
A vade-mecum for molecular biologists, Sambrook et al., Editors, "Molecular Cloning", A Laboratory Manual, 2nd Edition, Cold Spring Harbor Laboratory press, Cold Spring Harbor, New York, 1989;, TIBTECH Jun. 1991, 9:213-214.

* cited by examiner

SEQUENCE LISTING

<160> NUMBER OF SEQ ID NOS: 14

<210> SEQ ID NO 1
<211> LENGTH: 496
<212> TYPE: PRT
<213> ORGANISM: Thermotoga neapolitana

<400> SEQUENCE: 1

```
Met Ile Asp Leu Lys Gln Tyr Glu Phe Trp Phe Leu Val Gly Ser Gln
1               5                   10                  15

Tyr Leu Tyr Gly Leu Glu Thr Leu Lys Lys Val Glu Gln Gln Ala Ser
            20                  25                  30

Arg Ile Val Glu Ala Leu Asn Asn Asp Pro Ile Phe Pro Ser Lys Ile
        35                  40                  45

Val Leu Lys Pro Val Leu Lys Asn Ser Ala Glu Ile Arg Glu Ile Phe
50                  55                  60

Glu Lys Ala Asn Ala Glu Pro Lys Cys Ala Gly Val Ile Val Trp Met
65                  70                  75                  80

His Thr Phe Ser Pro Ser Lys Met Trp Ile Arg Gly Leu Ser Ile Asn
                85                  90                  95

Lys Lys Pro Leu Leu His Leu His Thr Gln Tyr Asn Arg Glu Ile Pro
            100                 105                 110

Trp Asp Thr Ile Asp Met Asp Tyr Met Asn Leu Asn Gln Ser Ala His
        115                 120                 125

Gly Asp Arg Glu His Gly Phe Ile His Ala Arg Met Arg Leu Pro Arg
130                 135                 140

Lys Val Val Gly His Trp Glu Asp Arg Glu Val Arg Glu Lys Ile
145                 150                 155                 160

Ala Lys Trp Met Arg Val Ala Cys Ala Ile Gln Asp Gly Arg Thr Gly
                165                 170                 175

Gln Ile Val Arg Phe Gly Asp Asn Met Arg Glu Val Ala Ser Thr Glu
            180                 185                 190

Gly Asp Lys Val Glu Ala Gln Ile Lys Leu Gly Trp Ser Ile Asn Thr
        195                 200                 205

Trp Gly Val Gly Glu Leu Ala Glu Arg Val Lys Ala Val Pro Glu Asn
210                 215                 220

Glu Val Glu Glu Leu Leu Lys Glu Tyr Lys Arg Tyr Ile Met Pro
225                 230                 235                 240

Glu Asp Glu Tyr Ser Leu Lys Ala Ile Arg Glu Gln Ala Lys Met Glu
                245                 250                 255

Ile Ala Leu Arg Glu Phe Leu Lys Glu Lys Asn Ala Ile Ala Phe Thr
            260                 265                 270

Thr Thr Phe Glu Asp Leu His Asp Leu Pro Gln Leu Pro Gly Leu Ala
        275                 280                 285

Val Gln Arg Leu Met Glu Glu Gly Tyr Gly Phe Gly Ala Glu Gly Asp
290                 295                 300

Trp Lys Ala Ala Gly Leu Val Arg Ala Leu Lys Val Met Gly Ala Gly
305                 310                 315                 320

Leu Pro Gly Gly Thr Ser Phe Met Glu Asp Tyr Thr Tyr His Leu Thr
                325                 330                 335

Pro Gly Asn Glu Leu Val Leu Gly Ala His Met Leu Glu Val Cys Pro
            340                 345                 350

Thr Ile Ala Lys Glu Lys Pro Arg Ile Glu Val His Pro Leu Ser Ile
        355                 360                 365

Gly Gly Lys Ala Asp Pro Ala Arg Leu Val Phe Asp Gly Gln Glu Gly
370                 375                 380

Pro Ala Val Asn Ala Ser Ile Val Asp Met Gly Asn Arg Phe Arg Leu
385                 390                 395                 400

Val Val Asn Arg Val Leu Ser Val Pro Ile Glu Arg Lys Met Pro Lys
```

```
                    405                 410                 415
Leu Pro Thr Ala Arg Val Leu Trp Lys Pro Leu Pro Asp Phe Lys Arg
            420                 425                 430

Ala Thr Thr Ala Trp Ile Leu Ala Gly Gly Ser His His Thr Ala Phe
        435                 440                 445

Ser Thr Ala Val Asp Val Glu Tyr Leu Ile Asp Trp Ala Glu Ala Leu
    450                 455                 460

Glu Ile Glu Tyr Leu Val Ile Asp Glu Asn Leu Asp Leu Glu Asn Phe
465                 470                 475                 480

Lys Lys Glu Leu Arg Trp Asn Glu Leu Tyr Trp Gly Leu Leu Lys Arg
                485                 490                 495

<210> SEQ ID NO 2
<211> LENGTH: 496
<212> TYPE: PRT
<213> ORGANISM: Thermotoga neapolitana

<400> SEQUENCE: 2

Met Ile Asp Leu Lys Gln Tyr Glu Phe Trp Phe Leu Val Gly Ser Gln
1               5                   10                  15

Tyr Leu Tyr Gly Leu Glu Thr Leu Lys Lys Val Glu Gln Gln Ala Ser
            20                  25                  30

Arg Ile Val Glu Ala Leu Asn Asn Asp Pro Ile Phe Pro Ser Lys Ile
        35                  40                  45

Val Leu Lys Pro Val Leu Lys Asn Ser Ala Glu Ile Arg Glu Ile Phe
    50                  55                  60

Glu Lys Ala Asn Ala Glu Pro Lys Cys Ala Gly Val Ile Val Trp Met
65                  70                  75                  80

His Thr Phe Ser Pro Ser Lys Met Trp Ile Arg Gly Leu Ser Ile Asn
                85                  90                  95

Lys Lys Pro Leu Leu His Leu His Thr Gln Tyr Asn Arg Glu Ile Pro
            100                 105                 110

Trp Asp Thr Ile Asp Met Asp Tyr Met Asn Leu Asn Gln Ser Ala His
        115                 120                 125

Gly Asp Arg Glu His Gly Phe Ile His Ala Arg Met Arg Leu Pro Arg
    130                 135                 140

Lys Val Val Gly His Trp Glu Asp Arg Glu Val Arg Glu Lys Ile
145                 150                 155                 160

Ala Lys Trp Met Arg Val Ala Cys Ala Ile Gln Asp Gly Arg Thr Gly
                165                 170                 175

Gln Ile Val Arg Phe Gly Asp Asn Met Arg Glu Val Ala Ser Thr Glu
            180                 185                 190

Gly Asp Lys Val Glu Ala Gln Ile Lys Leu Gly Trp Ser Ile Asn Thr
        195                 200                 205

Trp Gly Val Gly Glu Leu Ala Glu Arg Val Lys Ala Val Pro Glu Asn
    210                 215                 220

Glu Val Glu Glu Leu Leu Lys Glu Tyr Lys Glu Arg Tyr Ile Met Pro
225                 230                 235                 240

Glu Asp Glu Tyr Ser Leu Lys Ala Ile Arg Glu Gln Ala Lys Met Glu
                245                 250                 255

Ile Ala Leu Arg Glu Phe Leu Lys Glu Lys Asn Ala Ile Ala Phe Thr
            260                 265                 270

Thr Thr Phe Glu Asp Leu His Asp Leu Pro Gln Leu Pro Gly Leu Ala
        275                 280                 285
```

-continued

```
Val Gln Arg Leu Met Glu Glu Gly Tyr Gly Phe Gly Ala Glu Gly Asp
    290                 295                 300
Trp Lys Ala Ala Gly Leu Val Arg Ala Leu Lys Val Met Gly Ala Gly
305                 310                 315                 320
Leu Pro Gly Gly Thr Ser Phe Met Glu Asp Tyr Thr Tyr His Leu Thr
                    325                 330                 335
Pro Gly Asn Glu Leu Val Leu Gly Ala His Met Leu Glu Val Cys Pro
                340                 345                 350
Thr Ile Ala Lys Glu Lys Pro Arg Ile Glu Val His Pro Leu Ser Ile
            355                 360                 365
Gly Gly Lys Ala Asp Pro Ala Arg Leu Val Phe Asp Gly Gln Glu Gly
370                 375                 380
Pro Ala Val Asn Ala Ser Ile Val Asp Met Gly Asn Arg Phe Arg Leu
385                 390                 395                 400
Val Val Asn Arg Val Leu Ser Val Pro Ile Glu Arg Lys Met Pro Lys
                    405                 410                 415
Leu Pro Thr Ala Arg Val Leu Trp Lys Pro Leu Pro Asp Phe Lys Arg
                420                 425                 430
Ala Thr Thr Ala Trp Ile Leu Ala Gly Gly Ser His His Thr Ala Phe
            435                 440                 445
Ser Thr Ala Val Asp Val Glu Tyr Leu Ile Asp Trp Ala Glu Ala Leu
450                 455                 460
Glu Ile Glu Tyr Pro Val Ile Asp Glu Asn Leu Asp Leu Glu Asn Phe
465                 470                 475                 480
Lys Lys Glu Leu Arg Trp Asn Glu Leu Tyr Trp Gly Leu Leu Lys Arg
                    485                 490                 495

<210> SEQ ID NO 3
<211> LENGTH: 496
<212> TYPE: PRT
<213> ORGANISM: Thermotoga neapolitana

<400> SEQUENCE: 3

Met Ile Asp Leu Lys Gln Tyr Glu Phe Trp Phe Leu Val Gly Ser Gln
1               5                   10                  15
Tyr Leu Tyr Gly Leu Glu Thr Leu Lys Lys Val Glu Gln Gln Ala Ser
                20                  25                  30
Arg Ile Val Glu Ala Leu Asn Asn Asp Pro Ile Phe Pro Ser Lys Ile
            35                  40                  45
Val Leu Lys Pro Val Leu Lys Asn Ser Ala Glu Ile Arg Glu Ile Phe
50                  55                  60
Glu Lys Ala Asn Ala Glu Pro Lys Cys Ala Gly Val Ile Val Trp Met
65                  70                  75                  80
His Thr Phe Ser Pro Ser Lys Met Trp Ile Arg Gly Leu Ser Ile Asn
                85                  90                  95
Lys Lys Pro Leu Leu His Leu His Thr Gln Tyr Asn Arg Glu Ile Pro
            100                 105                 110
Trp Asp Thr Ile Asp Met Asp Tyr Met Asn Leu Asn Gln Ser Ala His
        115                 120                 125
Gly Asp Arg Glu His Gly Phe Ile His Ala Arg Met Arg Leu Pro Arg
130                 135                 140
Lys Val Val Val Gly His Trp Glu Asp Arg Glu Val Arg Glu Lys Ile
145                 150                 155                 160
Ala Lys Trp Met Arg Val Ala Cys Ala Ile Gln Asp Gly Arg Thr Gly
                165                 170                 175
```

Gln Ile Val Arg Phe Gly Asp Asn Met Arg Glu Val Ala Ser Thr Glu
                180                 185                 190

Gly Asp Lys Val Glu Ala Gln Ile Lys Leu Gly Trp Ser Ile Asn Thr
            195                 200                 205

Trp Gly Val Gly Glu Leu Ala Glu Arg Val Lys Ala Val Pro Glu Asn
210                 215                 220

Glu Val Glu Glu Leu Leu Lys Glu Tyr Lys Glu Arg Tyr Ile Met Pro
225                 230                 235                 240

Glu Asp Glu Tyr Ser Leu Lys Ala Ile Arg Glu Gln Ala Lys Met Glu
                245                 250                 255

Ile Ala Leu Arg Glu Phe Leu Lys Glu Lys Asn Ala Ile Ala Phe Thr
                260                 265                 270

Thr Thr Val Glu Asp Leu His Asp Leu Pro Gln Leu Pro Gly Leu Ala
            275                 280                 285

Val Gln Arg Leu Met Glu Glu Gly Tyr Gly Phe Gly Ala Glu Gly Asp
        290                 295                 300

Trp Lys Ala Ala Gly Leu Val Arg Ala Leu Lys Val Met Gly Ala Gly
305                 310                 315                 320

Leu Pro Gly Gly Thr Ser Phe Met Glu Asp Tyr Thr Tyr His Leu Thr
                325                 330                 335

Pro Gly Asn Glu Leu Val Leu Gly Ala His Met Leu Glu Val Cys Pro
                340                 345                 350

Thr Ile Ala Lys Glu Lys Pro Arg Ile Glu Val His Pro Leu Ser Ile
            355                 360                 365

Gly Gly Lys Ala Asp Pro Ala Arg Leu Val Phe Asp Gly Gln Glu Gly
        370                 375                 380

Pro Ala Val Asn Ala Ser Ile Val Asp Met Gly Asn Arg Phe Arg Leu
385                 390                 395                 400

Val Val Asn Arg Val Leu Ser Val Pro Ile Glu Arg Lys Met Pro Lys
                405                 410                 415

Leu Pro Thr Ala Arg Val Leu Trp Lys Pro Leu Pro Asp Phe Lys Arg
                420                 425                 430

Ala Thr Thr Ala Trp Ile Leu Ala Gly Gly Ser His His Thr Ala Phe
            435                 440                 445

Ser Thr Ala Val Asp Val Glu Tyr Leu Ile Asp Trp Ala Glu Ala Leu
        450                 455                 460

Glu Ile Glu Tyr Pro Val Ile Asp Glu Asn Leu Asp Leu Glu Asn Phe
465                 470                 475                 480

Lys Lys Glu Leu Arg Trp Asn Glu Leu Tyr Trp Gly Leu Leu Lys Arg
                485                 490                 495

<210> SEQ ID NO 4
<211> LENGTH: 496
<212> TYPE: PRT
<213> ORGANISM: Thermotoga neapolitana

<400> SEQUENCE: 4

Met Ile Asp Leu Lys Gln Tyr Glu Phe Trp Phe Leu Val Gly Ser Gln
1               5                   10                  15

Tyr Leu Tyr Gly Leu Glu Thr Leu Lys Lys Val Glu Gln Gln Ala Ser
            20                  25                  30

Arg Ile Val Glu Ala Leu Asn Asn Asp Pro Ile Phe Pro Ser Lys Ile
        35                  40                  45

Val Leu Lys Pro Val Leu Lys Asn Ser Ala Glu Ile Arg Glu Ile Phe

-continued

```
                50                  55                  60
Glu Lys Ala Asn Ala Glu Pro Lys Cys Ala Gly Val Ile Val Trp Met
 65                  70                  75                  80

His Thr Phe Ser Pro Ser Lys Met Trp Ile Arg Gly Leu Ser Ile Asn
                     85                  90                  95

Lys Lys Pro Leu Leu His Leu His Thr Gln Tyr Asn Arg Glu Ile Pro
                    100                 105                 110

Trp Asp Thr Ile Asp Met Asp Tyr Met Asn Leu Asn Gln Ser Ala His
                    115                 120                 125

Gly Asp Arg Glu His Gly Phe Ile His Ala Arg Met Arg Leu Pro Arg
                130                 135                 140

Lys Val Val Gly His Trp Glu Asp Arg Glu Val Arg Glu Lys Ile
145                 150                 155                 160

Ala Lys Trp Met Arg Val Ala Cys Ala Ile Gln Asp Gly Arg Thr Gly
                    165                 170                 175

Gln Ile Val Arg Phe Gly Asp Asn Met Arg Glu Val Ala Ser Thr Glu
                    180                 185                 190

Gly Asp Lys Val Glu Ala Gln Ile Lys Leu Gly Trp Ser Ile Asn Thr
                195                 200                 205

Trp Gly Val Gly Glu Leu Ala Glu Arg Val Lys Ala Val Pro Glu Asn
210                 215                 220

Glu Val Glu Leu Leu Lys Gly Tyr Lys Glu Arg Tyr Ile Met Pro
225                 230                 235                 240

Glu Asp Glu Tyr Ser Leu Lys Ala Ile Arg Glu Gln Ala Lys Met Glu
                    245                 250                 255

Ile Ala Leu Arg Glu Phe Leu Lys Glu Lys Asn Ala Ile Ala Phe Thr
                260                 265                 270

Thr Thr Met Glu Asp Leu His Asp Leu Pro Gln Leu Pro Gly Leu Ala
                    275                 280                 285

Val Gln Arg Leu Met Glu Glu Gly Tyr Gly Phe Gly Ala Glu Gly Asp
                290                 295                 300

Trp Lys Ala Ala Gly Leu Val Arg Ala Leu Lys Val Met Gly Ala Gly
305                 310                 315                 320

Leu Pro Gly Gly Thr Ser Phe Met Glu Asp Tyr Thr Tyr His Leu Thr
                    325                 330                 335

Pro Gly Asn Glu Leu Val Leu Gly Ala His Met Leu Glu Val Cys Pro
                340                 345                 350

Thr Ile Ala Lys Glu Lys Pro Arg Ile Glu Val His Pro Leu Ser Ile
                355                 360                 365

Gly Gly Lys Ala Asp Pro Ala Arg Leu Val Phe Asp Gly Gln Glu Gly
                370                 375                 380

Pro Ala Val Asn Ala Ser Ile Val Asp Met Gly Asn Arg Phe Arg Leu
385                 390                 395                 400

Val Val Asn Arg Val Leu Ser Val Pro Ile Glu Arg Lys Met Pro Lys
                    405                 410                 415

Leu Pro Thr Ala Arg Val Leu Trp Lys Pro Leu Pro Asp Phe Lys Arg
                420                 425                 430

Ala Thr Thr Ala Trp Ile Leu Ala Gly Gly Ser His His Thr Ala Phe
                435                 440                 445

Ser Thr Ala Val Asp Val Glu Tyr Leu Ile Asp Trp Ala Glu Ala Leu
                450                 455                 460

Glu Ile Glu Tyr Pro Val Ile Asp Glu Asn Leu Asp Leu Glu Asn Phe
465                 470                 475                 480
```

```
Lys Lys Glu Leu Arg Trp Asn Glu Leu Tyr Trp Gly Leu Leu Lys Arg
                485                 490                 495

<210> SEQ ID NO 5
<211> LENGTH: 496
<212> TYPE: PRT
<213> ORGANISM: Thermotoga neapolitana

<400> SEQUENCE: 5

Met Ile Asp Leu Lys Gln Tyr Glu Phe Trp Phe Leu Val Gly Ser Gln
1               5                   10                  15

Tyr Leu Tyr Gly Leu Glu Thr Leu Lys Lys Val Glu Gln Gln Ala Ser
                20                  25                  30

Arg Ile Val Glu Ala Leu Asn Asn Asp Pro Ile Phe Pro Ser Lys Ile
            35                  40                  45

Val Leu Lys Pro Val Leu Lys Asn Ser Ala Glu Ile Arg Glu Ile Phe
        50                  55                  60

Glu Lys Ala Asn Ala Glu Pro Lys Cys Ala Gly Val Ile Val Trp Met
65                  70                  75                  80

His Thr Phe Ser Pro Ser Lys Met Trp Ile Arg Gly Leu Ser Ile Asn
                85                  90                  95

Lys Lys Pro Leu Leu His Leu His Thr Gln Tyr Asn Arg Glu Ile Pro
                100                 105                 110

Trp Asp Thr Ile Asp Met Asp Tyr Met Asn Leu Asn Gln Ser Ala His
            115                 120                 125

Gly Asp Arg Glu His Gly Phe Ile His Ala Arg Met Arg Leu Pro Arg
        130                 135                 140

Lys Val Val Gly His Trp Glu Asp Arg Glu Val Arg Glu Lys Ile
145                 150                 155                 160

Ala Lys Trp Met Arg Val Ala Cys Ala Ile Gln Asp Gly Arg Thr Gly
                165                 170                 175

Gln Ile Val Arg Phe Gly Asp Asn Met Arg Glu Val Ala Ser Thr Glu
            180                 185                 190

Gly Asp Lys Val Glu Ala Gln Ile Lys Leu Gly Trp Ser Ile Asn Thr
        195                 200                 205

Trp Gly Val Gly Glu Leu Ala Glu Arg Val Lys Ala Val Pro Glu Asn
210                 215                 220

Glu Val Glu Glu Leu Leu Lys Glu Tyr Lys Glu Arg Tyr Ile Met Pro
225                 230                 235                 240

Glu Asp Glu Tyr Ser Leu Lys Ala Ile Arg Glu Gln Ala Lys Met Glu
                245                 250                 255

Ile Ala Leu Arg Glu Phe Leu Lys Glu Lys Asn Ala Ile Ala Phe Thr
            260                 265                 270

Thr Thr Ile Glu Asp Leu His Asp Leu Pro Gln Leu Pro Gly Leu Ala
        275                 280                 285

Val Gln Arg Leu Met Glu Glu Gly Tyr Gly Phe Gly Ala Glu Gly Asp
        290                 295                 300

Trp Lys Ala Ala Gly Leu Val Arg Ala Leu Lys Val Met Gly Ala Gly
305                 310                 315                 320

Leu Pro Gly Gly Thr Ser Phe Met Glu Asp Tyr Thr Tyr His Leu Thr
                325                 330                 335

Pro Gly Asn Glu Leu Val Leu Gly Ala His Met Leu Glu Val Cys Pro
            340                 345                 350

Thr Ile Ala Lys Glu Lys Pro Arg Ile Glu Val His Pro Leu Ser Ile
```

```
                355                 360                 365
Gly Gly Lys Ala Asp Pro Ala Arg Leu Val Phe Asp Gly Gln Glu Gly
            370                 375                 380

Pro Ala Val Asn Ala Ser Ile Val Asp Met Gly Asn Arg Phe Arg Leu
385                 390                 395                 400

Val Val Asn Arg Val Leu Ser Val Pro Ile Glu Arg Lys Met Pro Lys
                405                 410                 415

Leu Pro Thr Ala Arg Val Leu Trp Lys Pro Leu Pro Asp Phe Lys Arg
            420                 425                 430

Ala Thr Thr Ala Trp Ile Leu Ala Gly Gly Ser His His Thr Ala Phe
            435                 440                 445

Ser Thr Ala Val Asp Val Glu Tyr Leu Ile Asp Trp Ala Glu Ala Leu
            450                 455                 460

Glu Ile Glu Tyr Pro Val Ile Asp Glu Asn Leu Asp Leu Glu Asn Phe
465                 470                 475                 480

Lys Lys Glu Leu Arg Trp Asn Glu Leu Tyr Trp Gly Leu Leu Lys Arg
                485                 490                 495

<210> SEQ ID NO 6
<211> LENGTH: 1491
<212> TYPE: DNA
<213> ORGANISM: Thermotoga neapolitana

<400> SEQUENCE: 6
atgatcgatc tcaaacagta tgagttctgg tttcttgtcg gcagccagta tctctacggt     60
ctggagacgt tgaagaaggt agagcagcag gcaagcagga tagttgaggc actgaacaat    120
gatcccattt ttccctcaaa gatcgttctg aaacccgttc tgaaaaattc cgccgagatc    180
agagagatct cgaaaaggc aaatgcagaa ccaaaatgcg ccggtgtcat cgtgtggatg    240
cacacgttct caccttcgaa gatgtggata gaggcctct ccatcaataa aaaccccctg     300
cttcacctcc acacccagta caacaggag atcccgtggg acacgatcga tatggactac    360
atgaacctga ccaatctgc ccacggtgac agggaacacg gattcattca cgcgaggatg    420
agactcccaa gaaggtcgt ggtgggacat tgggaagaca gagaagtcag ggaaaagatc    480
gcaaaatgga tgagagtggc ctgcgcgata caggatggaa gaactggaca gatcgtgaga    540
ttcggcgata acatgagaga ggttgccagc accgaaggag acaaggtgga ggcacagata    600
aaactcggct ggtccataaa cacctggggt gtcggagagc tcgccgagag agtgaaggcg    660
gttccagaaa acgaagtgga ggaattgttg aaggagtaca agaaaggta catcatgcca    720 gaagacgaat acagcctcaa agcgatcaga gaacaggcga gatggagat tgcactgaga    780 gagtttctga agagaagaa tgccatcgcc ttcaccacca ccttcgagga tcttcacgat    840
cttccccagc ttcccggtct tgcagtccag aggctcatgg aggaagggta tggatttgga    900
gcggaaggag actggaaggc agccgggctt gtgagggctt tgaaggtcat gggagctggt    960
cttcccggtg gtacatcctt catggaggac tacacctacc atctcacacc gggaaacgaa   1020
ctcgtgctgg gagcgcacat gctagaggtg tgccccacga tcgctaagga aaagccaaga   1080
atagaggtgc atcctctcag catcggtgga aaagcagatc ctgcacgcct tgttttcgat   1140
ggacaagaag gtcccgctgt caacgcctcc atcgttgaca tgggaaacag gttcaggctg   1200
gtagtgaaca gagtgttgtc cgttcccatt gaaaggaaga tgcccaaact tccaacggca   1260
agagttttgt ggaagccgct tcctgatttc aagagggcga cgactgcgtg gattctcgct   1320
ggaggatccc atcatactgc cttctcaaca gcggtggatg tggagtacct catcgactgg   1380
```

```
gcggaggctt tggagataga gtatcttgtc atcgatgaaa atctggatct ggagaacttc    1440
aaaaaggaac tgagatggaa cgaactctac tggggacttt taaaaagatg a            1491
```

<210> SEQ ID NO 7
<211> LENGTH: 1491
<212> TYPE: DNA
<213> ORGANISM: Thermotoga neapolitana

<400> SEQUENCE: 7

```
atgatcgatc tcaaacagta tgagttctgg tttcttgtcg gcagccagta tctctacggt     60
ctggagacgt tgaagaaggt agagcagcag gcaagcagga tagttgaggc actgaacaat    120
gatcccattt ttccctcaaa gatcgttctg aaacccgttc tgaaaaattc cgccgagatc    180
agagagatct tcgaaaaggc aaatgcagaa ccaaaatgcg ccggtgtcat cgtgtggatg    240
cacacgttct caccttcgaa gatgtggata agaggcctct ccatcaataa aaaaccccctg    300 cttcacctcc acacccagta caacaggag atcccgtggg acacgatcga tatggactac    360
atgaacctga ccaatctgc ccacggtgac agggaacacg gattcattca cgcgaggatg    420
agactcccaa gaaggtcgt ggtgggacat tgggaagaca gagaagtcag ggaaaagatc    480
gcaaaatgga tgagagtggc ctgcgcgata caggatggaa gaactggaca gatcgtgaga    540
ttcggcgata acatgagaga ggttgccagc accgaaggag acaaggtgga ggcacagata    600
aaactcggct ggtccataaa cacctggggt gtcggagagc tcgccgagag agtgaaggcg    660
gttccagaaa acgaagtgga ggaattgttg aaggagtaca agaaaggta catcatgcca    720 gaagacgaat acagcctcaa agcgatcaga gaacaggcga gatggagat tgcactgaga    780 gagtttctga agagaagaa tgccatcgcc ttcaccacca ccttcgagga tcttcacgat    840
cttccccagc ttcccggtct tgcagtccag aggctcatgg aggaagggta tggatttgga    900
gcggaaggag actggaaggc agccgggctt gtgagggctt tgaaggtcat gggagctggt    960
cttcccggtg gtacatcctt catggaggac tacacctacc atctcacacc gggaaacgaa    1020
ctcgtgctgg gagcgcacat gctagaggtg tgccccacga tcgctaagga aaagccaaga    1080
atagaggtgc atcctctcag catcggtgga aaagcagatc ctgcacgcct tgttttcgat    1140
ggacaagaag gtccogctgt caacgcctcc atcgttgaca tgggaaacag gttcaggctg    1200
gtagtgaaca gagtgtttgtc cgttcccatt gaaaggaaga tgcccaaact tccaacggca    1260
agagttttgt ggaagccgct tcctgatttc aagagggcga cgactgcgtg gattctcgct    1320
ggaggatccc atcatactgc cttctcaaca gcggtggatg tggagtacct catcgactgg    1380
gcggaggctt tggagataga gtatcctgtc atcgatgaaa atctggatct ggagaacttc    1440
aaaaaggaac tgagatggaa cgaactctac tggggacttt taaaaagatg a              1491
```

<210> SEQ ID NO 8
<211> LENGTH: 1491
<212> TYPE: DNA
<213> ORGANISM: Thermotoga neapolitana

<400> SEQUENCE: 8

```
atgatcgatc tcaaacagta tgagttctgg tttcttgtcg gcagccagta tctctacggt     60
ctggagacgt tgaagaaggt agagcagcag gcaagcagga tagttgaggc actgaacaat    120
gatcccattt ttccctcaaa gatcgttctg aaacccgttc tgaaaaattc cgccgagatc    180
agagagatct tcgaaaaggc aaatgcagaa ccaaaatgcg ccggtgtcat cgtgtggatg    240
```

```
cacacgttct caccttcgaa gatgtggata agaggcctct ccatcaataa aaaacccctg      300
cttcacctcc acacccagta caacagggag atcccgtggg acacgatcga tatggactac      360
atgaacctga accaatctgc ccacggtgac agggaacacg gattcattca cgcgaggatg      420
agactcccaa gaaaggtcgt ggtgggacat tgggaagaca gagaagtcag ggaaaagatc      480
gcaaaatgga tgagagtggc ctgcgcgata caggatggaa gaactggaca gatcgtgaga      540
ttcggcgata acatgagaga ggttgccagc accgaaggag acaaggtgga ggcacagata      600
aaactcggct ggtccataaa cacctggggt gtcggagagc tcgccgagag agtgaaggcg      660
gttccagaaa acgaagtgga ggaattgttg aaggagtaca agaaaggta catcatgcca      720 gaagacgaat acagcctcaa agcgatcaga gaacaggcga gatggagat tgcactgaga       780 gagtttctga agagaagaa tgccatcgcc ttcaccacca ccgttgagga tcttcacgat        840
cttccccagc ttcccggtct tgcagtccag aggctcatgg aggaaggta tggatttgga        900 gcggaaggag actggaaggc agccgggctt gtgagggctt tgaaggtcat gggagctggt      960
cttcccggtg gtacatcctt catggaggac tacacctacc atctcacacc gggaaacgaa    1020
ctcgtgctgg gagcgcacat gctagaggtg tgccccacga tcgctaagga aaagccaaga    1080
atagaggtgc atcctctcag catcggtgga aaagcagatc ctgcacgcct tgttttcgat    1140
ggacaagaag gtcccgctgt caacgcctcc atcgttgaca tgggaaacag gttcaggctg    1200
gtagtgaaca gagtgttgtc cgttcccatt gaaaggaaga tgcccaaact tccaacggca    1260
agagttttgt ggaagccgct tcctgatttc aagagggcga cgactgcgtg gattctcgct    1320
ggaggatccc atcatactgc cttctcaaca gcggtggatg tggagtacct catcgactgg    1380
gcggaggctt tggagataga gtatcctgtc atcgatgaaa atctggatct ggagaacttc    1440
aaaaaggaac tgagatggaa cgaactctac tggggacttt taaaaagatg a             1491
```

<210> SEQ ID NO 9
<211> LENGTH: 1491
<212> TYPE: DNA
<213> ORGANISM: Thermotoga neapolitana

<400> SEQUENCE: 9

```
atgatcgatc tcaaacagta tgagttctgg tttcttgtcg gcagccagta tctctacggt       60
ctggagacgt tgaagaaggt agagcagcag gcaagcagga tagttgaggc actgaacaat      120
gatcccattt ttccctcaaa gatcgttctg aaacccgttc tgaaaaattc cgccgagatc      180
agagagatct tcgaaaaggc aaatgcagaa ccaaaatgcg ccggtgtcat cgtgtggatg      240
cacacgttct caccttcgaa gatgtggata agaggcctct ccatcaataa aaaacccctg      300
cttcacctcc acacccagta caacagggag atcccgtggg acacgatcga tatggactac      360
atgaacctga accaatctgc ccacggtgac agggaacacg gattcattca cgcgaggatg      420
agactcccaa gaaaggtcgt ggtgggacat tgggaagaca gagaagtcag ggaaaagatc      480
gcaaaatgga tgagagtggc ctgcgcgata caggatggaa gaactggaca gatcgtgaga      540
ttcggcgata acatgagaga ggttgccagc accgaaggag acaaggtgga ggcacagata      600
aaactcggct ggtccataaa cacctggggt gtcggagagc tcgccgagag agtgaaggcg      660
gttccagaaa acgaagtgga ggaattgttg aaggagtaca agaaaggta catcatgcca       720 gaagacgaat acagcctcaa agcgatcaga gaacaggcga gatggagat tgcactgaga       780 gagtttctga agagaagaa tgccatcgcc ttcaccacca ccatggagga tcttcacgat       840
cttccccagc ttcccggtct tgcagtccag aggctcatgg aggaaggta tggatttgga       900
```

```
gcggaaggag actggaaggc agccgggctt gtgagggctt tgaaggtcat gggagctggt    960
cttcccggtg gtacatcctt catggaggac tacacctacc atctcacacc gggaaacgaa    1020
ctcgtgctgg gagcgcacat gctagaggtg tgccccacga tcgctaagga aaagccaaga    1080
atagaggtgc atcctctcag catcggtgga aaagcagatc ctgcacgcct tgttttcgat    1140
ggacaagaag gtcccgctgt caacgcctcc atcgttgaca tgggaaacag gttcaggctg    1200
gtagtgaaca gagtgttgtc cgttcccatt gaaaggaaga tgcccaaact tccaacggca    1260
agagttttgt ggaagccgct tcctgatttc aagagggcga cgactgcgtg gattctcgct    1320
ggaggatccc atcatactgc cttctcaaca gcggtggatg tggagtacct catcgactgg    1380
gcggaggctt tggagataga gtatcctgtc atcgatgaaa atctggatct ggagaacttc    1440
aaaaaggaac tgagatggaa cgaactctac tggggacttt taaaaagatg a             1491
```

<210> SEQ ID NO 10
<211> LENGTH: 1491
<212> TYPE: DNA
<213> ORGANISM: Thermotoga neapolitana

<400> SEQUENCE: 10

```
atgatcgatc tcaaacagta tgagttctgg tttcttgtcg gcagccagta tctctacggt     60
ctggagacgt tgaagaaggt agagcagcag gcaagcagga tagttgaggc actgaacaat    120
gatcccattt ttccctcaaa gatcgttctg aaacccgttc tgaaaaattc cgccgagatc    180
agagagatct tcgaaaaggc aaatgcagaa ccaaaatgcg ccggtgtcat cgtgtggatg    240
cacacgttct caccttcgaa gatgtggata agaggcctct ccatcaataa aaaacccctg    300
cttcacctcc acacccagta caacaggagg atcccgtggg acacgatcga tatggactac    360
atgaacctga ccaatctgcc ccacggtgac agggaacacg gattcattca cgcgaggatg    420
agactcccaa gaaaggtcgt ggtgggacat tgggaagaca gagaagtcag ggaaaagatc    480
gcaaaatgga tgagagtggc ctgcgcgata caggatggaa gaactggaca gatcgtgaga    540
ttcggcgata acatgagaga ggttgccagc accgaaggag acaaggtgga ggcacagata    600
aaactcggct ggtccataaa cacctggggt gtcggagagc tcgccgagag agtgaaggcg    660
gttccagaaa acgaagtgga ggaattgttg aaggagtaca agaaaggta catcatgcca    720
gaagacgaat acagcctcaa agcgatcaga gaacaggcga gatggagat tgcactgaga    780
gagtttctga agagaagaa tgccatcgcc ttcaccacca ccatcgagga tcttcacgat    840
cttccccagc ttcccggtct tgcagtccag aggctcatgg aggaaggta tggatttgga    900
gcggaaggag actggaaggc agccgggctt gtgagggctt tgaaggtcat gggagctggt    960
cttcccggtg gtacatcctt catggaggac tacacctacc atctcacacc gggaaacgaa    1020
ctcgtgctgg gagcgcacat gctagaggtg tgccccacga tcgctaagga aaagccaaga    1080
atagaggtgc atcctctcag catcggtgga aaagcagatc ctgcacgcct tgttttcgat    1140
ggacaagaag gtcccgctgt caacgcctcc atcgttgaca tgggaaacag gttcaggctg    1200
gtagtgaaca gagtgttgtc cgttcccatt gaaaggaaga tgcccaaact tccaacggca    1260
agagttttgt ggaagccgct tcctgatttc aagagggcga cgactgcgtg gattctcgct    1320
ggaggatccc atcatactgc cttctcaaca gcggtggatg tggagtacct catcgactgg    1380
gcggaggctt tggagataga gtatcctgtc atcgatgaaa atctggatct ggagaacttc    1440
aaaaaggaac tgagatggaa cgaactctac tggggacttt taaaaagatg a             1491
```

```
<210> SEQ ID NO 11
<211> LENGTH: 45
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 11
ccatcgcctt caccaccacc nnsgaggatc ttcacgatct tcccc          45

<210> SEQ ID NO 12
<211> LENGTH: 45
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 12
ggggaagatc gtgaagatcc tcsnnggtgg tggtgaaggc gatgg          45

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
ggatcccata ctcctttctc aacagag                              27

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
cgctgttgag aaaggagtat gatgggatcc                           30
```

L-ARABINOSE ISOMERASE VARIANTS WITH IMPROVED CONVERSION ACTIVITY AND METHOD FOR PRODUCTION OF D-TAGATOSE USING THEM

CROSS REFERENCE TO RELATED APPLICATIONS

This application is a National Stage Entry of International Application No. PCT/KR2014/003658 filed on Apr. 25, 2014 (WO 2015/133678), and claims the benefit of PCT/KR2014/001789, filed on Mar. 5, 2014, which is hereby incorporated by reference in its entirety for all purposes as if fully set forth herein.

TECHNICAL FIELD

The present invention relates to an L-arabinose isomerase variant from *Thermotoga neapolitana* DSM 5068, which is produced by protein engineering and has an increased activity of converting D-galactose into D-tagatose, a microorganism that expresses the L-arabinose isomerase variant, and a method of producing D-tagatose from D-galactose using the microorganism.

Incorporated by reference herein in its entirety is the Sequence Listing entitled "Sequence List.txt", created Jul. 12, 2016 size of 33 kilobytes.

BACKGROUND ART

D-tagatose is a monosaccharide that has sweetness equal to about 90% of that of sugar while having properties, including low calorie and non-carious properties. It can be used as a healthy sweetener without causing various adult diseases, unlike conventional sweeteners.

Due to such properties, D-tagatose is receiving as a substitute for sugar and is known to have high market potential in the food market. However, tagatose is a rare sugar that is not abundantly present in nature, but is contained in milk products or some plants in very small amounts. For this reason, in order for tagatose to be used as a low-calorie functional sweetener, technology capable of producing tagatose should be developed.

D-tagatose was produced by a chemical isomerization process from D-galactose using $Ca(OH)_2$ as a catalyst by Arla Foods Ingredients Inc. in 2003, and has been marketed under the brand name "Gaio-tagatose". However, it is known that the chemical isomerization process is excellent in terms of isomerization conversion yield, but has shortcomings in that recovery and purification are difficult and the process is complex, and thus the total yield of the process is lower than that of an enzymatic isomerization process.

L-arabinose isomerase (EC 5.3.1.5) is an enzyme that catalyzes an isomerization reaction of converting L-arabinose into L-ribulose. In addition, it is known that L-arabinose isomerase converts not only L-arabinose (that is the natural substrate thereof) into L-ribulose, but also D-galactose (that is a substrate structurally similar to L-arabinose) into D-tagatose.

The most important factor capable of contributing to an increase in the productivity of a process of producing D-tagatose from D-galactose using L-arabinose isomerase is to develop an enzyme, which has good reactivity and can be successfully applied to the production process, through the modification of isomerase. Because an increase in productivity plays a crucial role in the maximization of profit by a decrease in production cost and the success of business, there has been a continued need to modify arabinose isomerase.

Arabinose isomerase from *Thermotoga neapolitana* DSM 5068 that is a thermophilic microorganism has a very high thermal stability, but needs to be further improved in order to ensure the economic productivity of arabinose isomerase, which is comparable to that of glucose isomerase.

Generally, methods of producing variant enzymes to increase the activities of enzymes or make enzymes active for new substrates are largely divided into a random mutagenesis method and a rational design method. The random mutagenesis method is widely used, because it can be used without requiring special information about a target enzyme. However, it requires a screening system capable of processing a very large number of variant enzymes. On the other hand, the modification of enzymes by rational design requires no special screening system, because it produces only a limited number of variant enzymes. However, in the case of rational design, factors that determine the catalytic mechanism, substrate binding property or substrate specificity of a target enzyme should be investigated in detail.

DISCLOSURE

Technical Problem

Accordingly, the applicant has attempted to increase the substrate specificity of L-arabinose isomerase from *Thermotoga neapolitana* DSM 5068 for D-galactose by changing the three-dimensional structure of L-arabinose isomerase on the basis of protein engineering, molecular modeling and enzymatic reaction mechanism analysis so that arabinose isomerase having potential to produce tagatose can have the ability to industrially produce tagatose.

It is an object of the present invention to provide an arabinose isomerase variant from *Thermotoga neapolitana* DSM 5068, which has increased conversion activity, and a gene nucleotide sequence encoding the variant.

Another object of the present invention is to provide a recombinant vector comprising the gene nucleotide sequence, and a microorganism of the genus *Corynebacterium* transformed with the recombinant vector.

Still another object of the present invention is to provide a method of producing D-tagatose from D-galactose using either the arabinose isomerase variant or the transformed microorganism or a culture of the transformed microorganism.

Technical Solution

In order to accomplish the above objects, the present invention provides an arabinose isomerase variant having an increased activity of converting D-galactose into D-tagatose, the arabinose isomerase variant having a substitution of proline for leucine at position 469 and a substitution of an amino acid other than phenylalanine for an amino acid at position 275 of arabinose isomerase from *Thermotoga neapolitana* DSM 5068, and a gene nucleotide sequence encoding the arabinose isomerase variant.

The present invention also provides a recombinant vector comprising the gene nucleotide sequence, and a microorganism of the genus *Corynebacterium* transformed with the recombinant vector.

The present invention also provides a method of producing D-tagatose from D-galactose using either the arabinose isomerase variant or the transformed microorganism or a culture of the transformed microorganism.

Advantageous Effects

According to the present invention, the production of D-tagatose can be increased using a microorganism of the genus *Corynebacterium* transformed with the novel arabinose isomerase variant or the gene nucleotide sequence encoding the arabinose isomerase variant, thereby reducing the production cost and the infrastructure investment.

MODE FOR INVENTION

Figure 1:
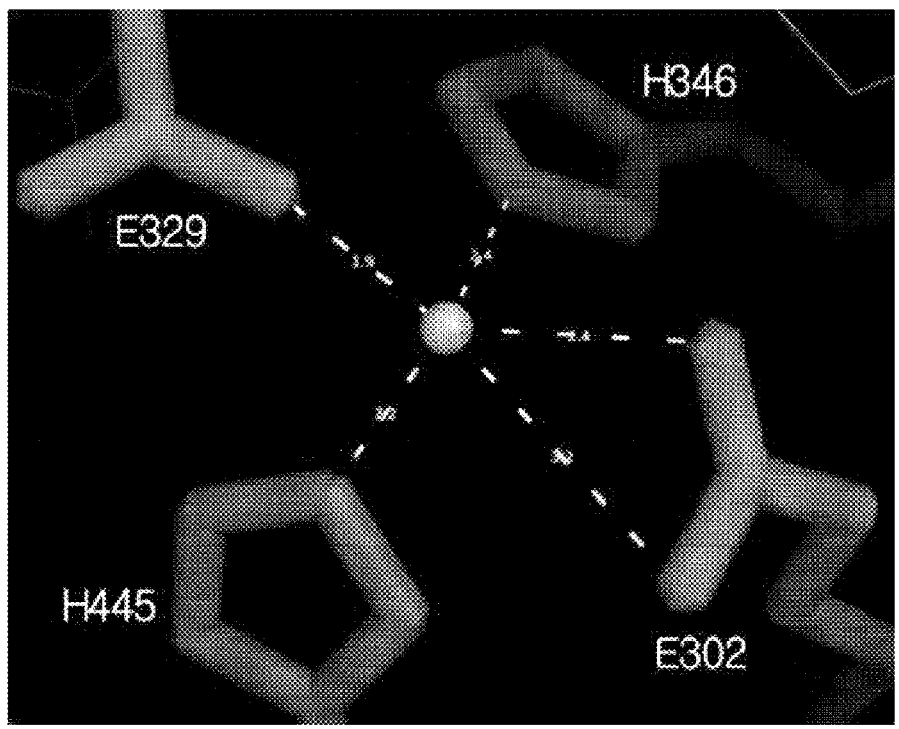
FIG. 1 shows a structure composed of the active site and co-factor manganese ion of L-arabinose isomerase from *Thermotoga neapolitana*.

In an embodiment, the present invention provides an arabinose isomerase variant from *Thermotoga neapolitana* DSM 5068, which has increased conversion activity, and a gene nucleotide sequence encoding the variant.

In a preferred embodiment, the present invention provides an arabinose isomerase variant having an increased activity of converting D-galactose into D-tagatose, the arabinose isomerase variant having a substitution of proline for leucine at position 469 and a substitution of an amino acid other than phenylalanine for an amino acid at position 275 of arabinose isomerase from *Thermotoga neapolitana* DSM 5068, and a gene nucleotide sequence encoding the arabinose isomerase variant.

As used herein, the expression "arabinose isomerase that converts D-galactose into D-tagatose" means an enzyme that catalyzes an isomerization reaction using D-galactose as a substrate to produce D-tagatose.

The arabinose isomerase variant according to the present invention preferably has a substitution of an amino acid having a nonpolar aliphatic side chain for an amino acid at position 275 of arabinose isomerase.

As used herein, the expression "amino acid having a nonpolar aliphatic side chain" means alanine, valine, isoleucine, leucine, methionine or proline.

Preferably, the amino acid at position 275 of arabinose isomerase is substituted with any one amino acid selected from the group consisting of valine, methionine and isoleucine.

Preferably, the arabinose isomerase variant according to the present invention further has a substitution of proline for leucine at position 469 of arabinose isomerase.

As used herein, the term "substitution" means substituting an amino acid at a specific position with another amino acid to make a mutation. A suitable mutagenesis method may be any method that can be used by those skilled in the art for this purpose. Particularly, the mutagenesis method may be a saturated mutagenesis method, a random mutagenesis method or a site-directed mutagenesis method (Evolutionary molecular engineering based on RNA replication, Pure Appl. Chem. 1984, 56:967-978; Promoters selected from random DNA-sequences, Proc. Natl. Acad. Sci. USA, 1986, 83:7405-7409; Mutants generated by the insertion of random oligonucleotides into the active-site of the beta-lactamase gene, Biochemistry 1989, 28:5703-5707).

Preferably, the arabinose isomerase variant according to the present invention has an amino acid at position 275, substituted using the saturated mutagenesis method, and leucine at position 469, substituted using the site-directed mutagenesis method.

In an embodiment of the present invention, random mutagenesis was performed using wild-type arabinose isomerase (having an amino acid sequence of SEQ ID NO: 1 and a nucleotide sequence of SEQ ID NO: 6) from *Thermotoga neapolitana* DSM 5068 as a template, thereby obtaining variants having improved enzymatic characteristics and genetic information about the variants. The variants were analyzed taken together, and as a result, it was found that variation in the amino acid sequence of the C-terminal region of arabinose isomerase influenced an increase in the enzymatic activity.

In addition, the amino acids in the C-terminal region constituting the active site of each of the wild-type arabinose isomerase and the arabinose isomerase variant were analyzed by molecular modeling. As a result, it was found that the variant had a substitution of proline for leucine at position 469 of the wild-type arabinose isomerase, and thus the beta-sheet at position 18 of the protein disappeared, and the angle of the backbone was slanted while the three-dimensional structure of the alpha-helix at position 17 moved toward the protein body, indicating that the structure of the protein was changed.

Based on the above-described results, leucine at position 469 of the wild-type arabinose isomerase was substituted with proline using the site-directed mutagenesis, thereby preparing a variant (L469P) (having an amino acid sequence of SEQ ID NO: 2 and a nucleotide sequence of SEQ ID NO: 7). The variant was incubated, and then the activity thereof was measured, and as a result, it was found that the variant showed a higher activity for the substrate galactose compared to the wild-type arabinose isomerase.

In an embodiment of the present invention, in order to obtain an enzyme having increased conversion activity from the arabinose isomerase variant (L469P), the major residues of the substrate binding region and active region of the enzyme were selected, and the reaction mechanism was estimated, thereby selecting the amino acid at position 275.

Mutations were introduced into position 275 using the saturated mutagenesis method, and the variants were screened, thereby selecting variants having increased conversion activity.

The selected variants were sequenced, and as a result, it was found that the variants had substitutions of valine (L469P/F275V), methionine (L469P/F275M) and isoleucine (L469P/F275I), respectively, for the amino acid at position 275. Each of the three variants was transformed into microorganisms of the genus *Corynebacterium*, and an isomerization reaction was performed by culturing the microorganisms. As a result, it was found that the three variants all showed increased activity compared to the variant L469P having a substitution of proline for leucine at position 469.

In order to examine the characteristics of the three variants, the expressed arabinose isomerases were isolated from the microorganisms of the genus *Corynebacterium* cultured under the above-described conditions. It was found that the purified proteins showed arabinose isomerase activity for D-galactose. In addition, it was found by SDS PAGE that the purified proteins had molecular weights consistent with that of arabinose isomerase.

Using the purified variant enzymes, the optimum temperature, thermal stability, metal ion usage and enzymatic activity of the variant enzymes were measured. As a result, it was found that the three variants showed the highest activity at 75° C., but the thermal stability somewhat decreased, the metal ion usage did not significantly differ, and the specific activities of the arabinose isomerase variants were about 5.5 times higher (F275V/L469P), 5 times higher (F275M/L469P) and 3.9 times higher (F275I/L469P), respectively, than that of the variant L469P.

In an embodiment, the present invention provides a gene nucleotide sequence encoding the arabinose isomerase variant.

The gene nucleotide sequence may be any one selected from the group consisting of SEQ ID NO: 8, SEQ ID NO: 9 and SEQ ID NO: 10.

The arabinose isomerase variants according to the present invention may have gene nucleotide sequences encoding proteins having a homology of at least 80%, preferably at least 90%, more preferably at least 95%, and particularly preferably at least 97%, to amino acid sequences of SEQ ID NOS: 3 to 5, as long as the arabinose isomerase activities of the arabinose isomerase variants of the present invention can be maintained or enhanced. Most preferably, the arabinose isomerase variants according to the present invention have gene nucleotide sequences set forth in SEQ ID NOS: 8 to 10.

As used herein, the term "homology" refers to the identity between two amino acid sequences. The homology can be determined using methods well known to those skilled in the art, for example, BLAST 2.0 which calculates parameters such as score, identity or similarity.

In addition, the polynucleotides according to the present invention may be variants encoding arabinose isomerase variants which can hybridize to polynucleotides set forth in SEQ ID NOS: 8 to 10 or probes from the polynucleotides under stringent conditions and which normally function.

As used herein, the term "stringent conditions" means conditions which permit specific hybridization between polynucleotides. For example, hybridization is performed in a hybridization buffer (3.5>SSC, 0.02% Ficoll, 0.02% polyvinylpyrrolidone, 0.02% bovine serum albumin, 2.5 mM NaH$_2$PO$_4$ (pH 7), 0.5% SDS, 2 mM EDTA) at 65° C. ("Molecular Cloning", A Laboratory Manual, J. Sambrook et al., Editors, 2nd Edition, Cold Spring Harbor Laboratory press, Cold Spring Harbor, N.Y., 1989) or Current Protocols in Molecular Biology (F. M. Ausubel et al., Editors, John Wiley & Sons, Inc., New York). Herein, SSC is 0.15 M sodium chloride/0.15 M sodium citrate (pH 7). After hybridization, the membrane having DNA transferred thereto is washed with 2>SSC at room temperature, and then washed with 0.1 to 0.5>SSC/0.1×SDS at a temperature of 68° C.

In an embodiment, the present invention provides an isomerase variant having any one amino acid sequence selected from the group consisting of SEQ ID NO: 3, SEQ ID NO: 4 and SEQ ID NO: 5. Specifically, the variant is an arabinose isomerase mutant having a substitution of any one amino acid selected from the group consisting of valine, methionine and isoleucine for an amino acid at position 275 and also having a substitution of proline for an amino acid at position 469.

However, the isomerase variant is not limited thereto, because the amino acid sequence of an enzyme showing the activity of the polypeptide may differ depending on the species or strain of microorganisms. Specifically, the variant of the present invention may be a mutant or artificial mutant encoding a polypeptide having an amino acid sequence comprising a substitution, deletion, insertion or addition of one or several amino acids at one or more positions other than positions 275 and 469 of the amino acid sequence of any one of SEQ ID NOS: 3 to 5, as long as the activity of arabinose isomerase can be maintained or enhanced.

As used herein, the term "several amino acids" means 2-20 amino acids, preferably 2-10 amino acids, and more preferably 2-5 amino acids, depending on the type or positions of amino acid residues in the three-dimensional structure of the protein.

Furthermore, the substitutions, deletions, insertions, additions, or inversions of amino acids may include naturally occurring mutants or artificial variants, based on individual differences and/or species differences of the microorganism expressing the arabinose isomerase.

In an embodiment, the present invention also provides a recombinant vector comprising a polynucleotide operably linked thereto.

As used herein, the term "vector" refers to a DNA construct containing the nucleotide sequence of a target protein-encoding gene operably linked to a suitable regulatory sequence so as to be able to express the target gene in a suitable host cell. The regulatory sequence includes a promoter capable of initiating transcription, any operator for regulating this transcription, a sequence encoding a suitable mRNA ribosome binding site, and a sequence for regulating the termination of transcription and translation. Once transformed into a suitable host, the vector may replicate or function independently of the host genome, or may integrate into the genome itself.

The vector that is used in the present invention is not specifically limited and may be any vector known in the art, as long as it can replicate in a host. Examples of the commonly used vectors may include natural or recombinant plasmids, cosmids, viruses, and bacteriophages.

Further, the vector that is used in the present invention is a vector capable of transforming host cells, to insert the polynucleotide encoding the target protein into the chromosome of the host cell. Specific examples of the vector include, but are not limited to, the shuttle vector pECCG112 that can self-replicate in both directions in *E. coli* and Coryne-type bacteria (Kap-Soo, Noh, Kor. Jour. Microbiol. July 1991, p 149-154).

Also, the polynucleotide encoding the endogenous target protein in the chromosome can be replaced with a new polynucleotide by a vector for insertion into the bacterial chromosome. Insertion of the polynucleotide into the chromosome can be performed by any method known in the art, for example, homologous recombination.

Because the vector of the present invention can be inserted into the chromosome by homologous recombination, it may further comprise a selection marker for confirming its insertion into the chromosome. The selection marker is used to select a cell transformed with the vector, that is, confirm the insertion of the target polynucleotide. The selection marker that is used in the present invention may be selected from markers that provide selectable phenotypes, such as drug resistance, auxotrophy, resistance to cytotoxic agents, or surface protein expression. Only cells expressing the selection marker are able to survive or to show different phenotypes under the environment treated with the selective agent, and thus the transformed cells can be selected.

In an embodiment, the present invention also provides a microorganism of the genus *Corynebacterium* transformed with the recombinant vector.

As used herein, the term "transformation" means introducing a vector comprising a polynucleotide encoding a target protein into a host cell so as to be able to express a protein encoded by the polynucleotide in the host cell. The transformed polynucleotides include all the genes inserted in the chromosome of the host cell or located outside the chromosome, as long as they can be expressed in the host cell. In addition, the polynucleotides include DNA and RNA, which encode the target protein. As long as the polynucleotide can be introduced in the host cell and expressed therein, the gene may be introduced in any form. For example, the polynucleotide can be introduced into the host cell in the form of an expression cassette which is a polynucleotide construct including all elements for expressing the gene. The expression cassette includes a promoter which is operably linked to the gene, a transcription termination signal, a ribosome binding site, and a translation termination signal. The expression cassette may be in the form of an expression vector capable of self-replicating. The polynucleotide may also be introduced into the host cell by itself, and be operably linked to the sequence necessary for expression in the host cell.

The microorganism of the present invention includes any of prokaryotic microorganisms and eukaryotic microorganisms, as long as it can express the isomerase variant. For example, it may include a microorganism belonging to the genus *Escherichia*, the genus *Erwinia*, the genus *Serratia*, the genus *Providencia*, the genus *Corynebacterium* or the genus *Brevibacterium*. Preferably, the microorganism of the present invention is a microorganism belonging to the genus *Corynebacterium*. More preferably, it is *Corynebacterium glutamicum*.

In an example of the present invention, *Corynebacterium glutamicum* having the ability to produce L-amino acid was transformed with a vector having a nucleotide sequence of each of SEQ ID NOS: 8, 9 and 10, and the constructed strains were named *Corynebacterium glutamicum* pFIS-1-TNAI-2, pFIS-1-TNAI-3 and pFIS-1-TNAI-4, respectively, and were deposited with the Korean Culture Center of Microorganisms (361-221, Honje 1-dong, Seodaemun-gu, Seoul, South Korea), an international depository authority, on Feb. 14, 2013 under the accession numbers KCCM11378P, KCCM11379P and KCCM11380P, respectively. In an embodiment, the present invention also provides a culture of a microorganism of the genus *Corynebacterium*.

The culture may be an undiluted culture comprising the cells of the microorganism or may be a microbial cell obtained by removing the supernatant of the culture or concentrating the culture. A medium composition for culturing the microorganism may comprise not only conventional components required for culture of microorganisms of the genus *Corynebacterium*, but also components having a synergistic effect on the growth of microorganisms of the genus *Corynebacterium*, and can be easily selected by those skilled in the art. In addition, the culture may be in a liquid or dry state, and methods for drying the culture include, but are not limited to, air drying, natural drying, spray-drying and freeze-drying.

The microorganism of the genus *Corynebacterium* according to the present invention can be cultured by any conventional method. Specifically, the microorganism can be cultured by inoculating it into a medium that totally or partially contains sucrose or glucose as a carbon source. The culture process can be performed in suitable media and culture conditions known in the art. This culture process can be easily modified by any person skilled in the art depending on the type of strain selected. Examples of the culture process include, but are not limited to, batch culture, continuous culture, and fed-batch culture. The medium that is used in culture of the microorganism of the present invention should properly satisfy the requirements of the microorganism of the present invention.

Specifically, the medium that is used in the present invention contains sucrose or glucose as a main carbon source. Further, molasses containing a high concentration of sucrose may also be used as a carbon source. In addition, suitable amounts of various carbon sources may be used. Preferably, purified glucose is used. Examples of nitrogen sources that may be used in the present invention include organic nitrogen sources such as peptone, yeast extract, meat extract, malt extract, corn steep liquor, and soy meal, and inorganic nitrogen sources such as urea, ammonium sulfate, ammonium chloride, ammonium phosphate, ammonium carbonate, and ammonium nitrate. Preferably, peptone is used. These nitrogen sources may be used alone or in combination. The medium may contain potassium phosphate monobasic, potassium phosphate dibasic and corresponding sodium-containing salts, as phosphorus sources. Further, the medium may contain a metal salt such as magnesium sulfate or iron sulfate. In addition, the medium may contain amino acids, vitamins and suitable precursors. These media or precursors may be added to the medium in a batch or continuous manner.

The culture medium is typically maintained at a temperature ranging from 27° C. to 37° C., and preferably from 30° C. to 37° C. Culture of the microorganism can be continued until the desired level of the protein will be obtained. Preferably the culture period is from 10 to 100 hours.

The present invention provides a method for producing D-tagatose, the method comprising reacting a solution containing D-galactose with a metal ion source selected from the group consisting of manganese ions, magnesium ions and zinc ions in the presence of the arabinose isomerase variant having an activity of converting D-galactose into D-tagatose, the transformed microorganism of the genus *Corynebacterium*, or a culture of the transformed microorganism of the genus *Corynebacterium*, thereby producing D-tagatose.

In order to enable a substrate to be introduced into the transformed microorganism of the genus *Corynebacterium*, or a culture of the transformed microorganism of the genus *Corynebacterium*, microbial cells obtained by centrifuging the transformed microorganism or the culture may be treated with a surfactant, lysozyme or xylene. Preferably, the microbial cells may be treated with 0.1% POESA.

The solution containing D-galactose, which is used in the present invention, may be selected from the group consisting of purified D-galactose, biomass-derived D-galactose, and D-galactose obtained by hydrolysis of lactose, but is not limited thereto.

The arabinose isomerase is a metalloenzyme that uses a metal ion as a cofactor. The metal ion may be selected from the group consisting of manganese ions, magnesium ions and zinc ions, but is not limited, and may be any metal ion that can bind to the isomerase to perform an isomerization reaction. Specifically, the manganese ion source includes manganese chloride; the magnesium ion source includes magnesium chloride; and the zinc ion source includes zinc chloride; however, the scope of the present invention are not limited to these metal ion sources.

A reaction solution for producing D-tagatose contains a buffer system for maintaining pH, such as Tris buffer or phosphate buffer. Preferably, it contains Tris buffer (pH 6.5 to 7.5). Manganese chloride, magnesium chloride or zinc chloride is contained at a concentration of 0.1 mM to 10 mM, and preferably 1 mM to 5 mM. The substrate D-galactose is added in an amount of 1 to 300 g/L, and preferably 18 to 300 g/L, and the isomerization reaction is induced at a temperature of 60° C. to 95° C., preferably 70° C. to 80° C., and more preferably 72° C. to 78° C., thereby producing D-tagatose.

Hereinafter, the present invention will be described in further detail with reference to examples. It will be obvious to those skilled in the art that these examples are for illustrative purposes only and are not intended to limit the scope of the present invention.

EXAMPLES

Example 1

Modeling of *Thermotoga neapolitana* Arabinose Isomerase Protein for Construction of Enzyme Having Increased Conversion Activity and Selection of Major Amino Acid Mutations Because the three-dimensional structure of wild-type arabinose isomerase from *Thermotoga neapolitana* DSM 5068 has not yet been found, prediction of the three-dimensional structure was performed by a molecular modeling technique using, as a template, *Escherichia coli* arabinose isomerase whose three-dimensional structure has already been found and which has a high sequence homology. For prediction of the three-dimensional structure, a comparative modeling technique was used, and a structural model was obtained using an APM module (Tripos, USA) in a molecular modeling package.

The comparative modeling technique is a method that is most frequently used to predict the three-dimensional structures of proteins. If the amino acid sequence of a desired protein is much similar to the sequence of another protein whose three-dimensional structure has been known, the three-dimensional structure of the desired protein can be easily predicted using the comparative modeling technique, and in this case, the accuracy of prediction is very high.

The structure of *E. coli* arabinose isomerase used in this Example was a trimer-type structure registered as 2HXG.pdb in the Protein Data Bank (PDB).

From the results of modeling, it was predicted that the wild-type arabinose isomerase (having an amino acid sequence of SEQ ID NO: 1 and a nucleotide sequence of SEQ ID NO: 6) from *Thermotoga neapolitana* DSM 5068 would very similar to the *E. coli* arabinose isomerase in terms of not only the nucleotide sequence, but also the two- and three-dimensional structures. Several studies on the *E. coli* arabinose isomerase reported information about the substrate binding site, the cofactor manganese ion ($Mn^{2+}$) and the major amino acids (Manjasetty & Chance, J. Mol. Biol., 2006. 360:297-309). Based on such information, the major residues of isomerase from *Thermotoga neapolitana* DSM 5068 were selected.

For analysis of the major amino acid residues, sequence alignment, molecular docking simulation, and reaction mechanism analysis, were performed. Sequence alignment was performed using clustalW algorithm (//www.ebi.ac.uk/Tools/msa/clustalw2/) based on information about the sequences of 10 different L-arabinose isomerases and *Thermotoga neapolitana* arabinose isomerase.

The results of the sequence alignment suggest that the sequences of the metal binding site and active site of arabinose isomerase from *Thermotoga neapolitana* DSM 5068 were very well conserved, like those of other isomerases. Isomerase from *Thermotoga neapolitana* DSM 5068 had an active site comprising E302 (glutamic acid at position 302), E329 (glutamic acid at position 329), H346 (histidine at position 346) and H445 (histidine at position 445) amino acid residues and manganese ions (FIG. 1), and the E302, E329, H346 and H445 amino acid residues had effects on manganese ion binding. Particularly, the E302 and E329 residues were predicted to be the most important factors that promote an isomerization reaction (Manjasetty & Chance, J. Mol. Biol., 2006. 360:297-309).

It was assumed that the substrate specificity of the *Thermotoga neapolitana* arabinose isomerase would be determined according to the size and morphology of the active site and the characteristics of the amino acid residues of the active site. Through molecular docking simulation (surflex-Dock; Tripos, USA) performed using the original substrate L-arabinose, residues important in substrate recognition were selected. In addition, through reaction mechanism analysis (Adrian J. Mulholland, Drug Discov. Today. 2005. 10(20):1393-402), the most suitable binding position of D-galactose was selected. Based on this selection, an amino acid residue having a high possibility of interfering with the binding between the active site of arabinose isomerase and D-galactose was selected.

Figure 2:
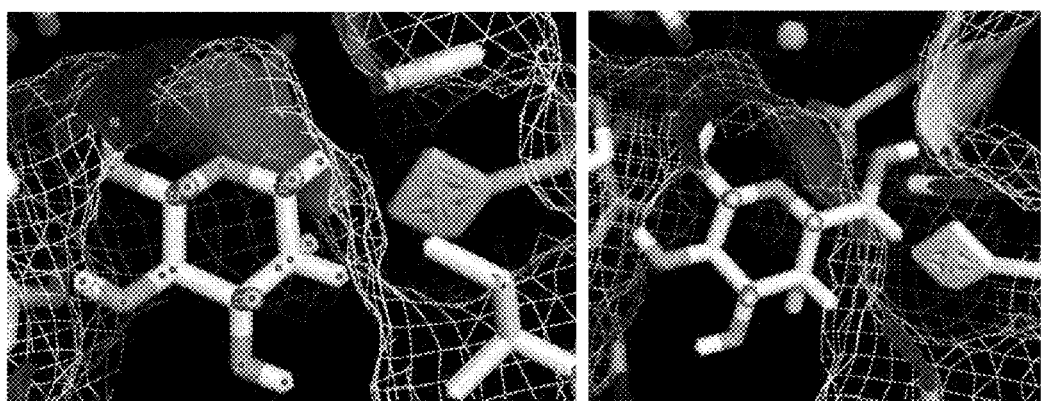
FIG. 2 shows the sites of L-arabinose and D-galactose, which bind to the active site of L-arabinose isomerase, and the functional groups of L-arabinose and D-galactose, which interact with the active site of L-arabinose isomerase. It shows that carbon 6 of D-galactose causes steric hindrance with the phenylalanine residue at position 275 of L-arabinose isomerase.

The amino acid at position 275 consisted of phenylalanine which has an aromatic side chain and is relatively large in size and less flexible, and it was predicted that the amino acid at position 275 would cause steric hindrance with carbon 6 of D-galactose (FIG. 2). Because L-arabinose, a pentose, shows substantially the same structure as D-galactose, except that the number of carbon atoms is smaller than that of D-galactose by one, it was anticipated that the reactivity of the arabinose isomerase with D-galactose could be significantly increased even by only the substitution of the amino acid at position 275 with other amino acid.

As amino acids capable of substituting phenylalanine, valine, methionine and isoleucine were selected, which have polarity to that of phenylalanine, are relatively small in size and highly flexible, and thus are predicted to have less effect on the overall structure of the arabinose isomerase while minimizing repulsion with carbon 6 of D-galactose.

Because these selected amino acids are composed of a nonpolar aliphatic chain, unlike phenylalanine comprising an aromatic chain, it was anticipated that these amino acids could substitute for phenylalanine while they would be structurally free.

The structures of variants (having amino acid sequences of SEQ ID NOS: 3 to 5 and nucleotide sequences of SEQ ID NOS: 8 to 10) having point mutations were predicted by a molecular modeling technique. As a result, it was predicted that the effect of the mutations on the overall structure of the arabinose isomerase would be insignificant.

In addition, through random mutagenesis performed using the wild-type arabinose isomerase from *Thermotoga neapolitana* DSM 5068 using a template, variants showing improved enzymatic characteristics and genetic information about the variants were obtained. The variants were analyzed taken together, and as a result, it was found that variation in the amino acid sequence of the C-terminal region of the arabinose isomerase had an increase in the enzymatic activity.

The phenomenon that the chain structure of the C-terminal region of the arabinose isomerase is greatly changed was analyzed by a molecular prediction technique. As a result, it was anticipated that the reactivity of the arabinose isomerase with D-galactose can be significantly increased even by only the substitution of proline for leucine at position 469 of the wild-type arabinose isomerase.

Example 2

Preparation of Designed Arabinose Isomerase Variants (1) Substitution of Proline for Leucine at Position 469

Leucine at position 469 of wild-type arabinose isomerase from *Thermotoga neapolitana* DSM 5068 was substituted with proline by a site-directed mutagenesis method using specific primers.

As the primers, an N-terminal primer (SEQ ID NO: 13) and a C-terminal primer (SEQ ID NO: 14), which are oligonucleotides having complementary nucleotide sequences with a mutation, were used. Using a plasmid DNA as a template, a plasmid having a new mutation was amplified and synthesized in a test tube, and then wild-type DNA was removed by cleavage with a Dpn I restriction enzyme. In other words, the wild-type DNA used as the template was a DNA isolated from *E. coli* and was digested with Dpn I that recognizes and cleaves Gm6ATC, but the DNA synthesized in the test tube was not cleaved.

The DNA was transformed into *E. coli* DH5 alpha to obtain a variant gene, and then the nucleotide sequence of the variant gene was analyzed to confirm that the mutation properly occurred. The variant gene was transformed into *Corynebacterium glutamicum* ATCC 13032 to produce a recombinant strain which was then named L469P. The recombinant strain was used as a control.

(2) Substitution of Amino Acid Other then Phenylalanine for Amino Acid at Position 259

In order to induce an additional mutation in the constructed variant L469P, a vector cloned with isomerase was subjected to saturated mutagenesis using a pair of primers containing a mutation.

The designed primer pair was designed such that the amino acid codon at position 275 would be substituted with NNS (N: A, T, G or C; and S: G or C). The variants obtained by this method may comprise 20 kinds of amino acids (SEQ ID NO: 11 and SEQ ID NO: 12). Such variants provided single colonies by transformation, and the changes in activity by the 20 amino acid mutations at the corresponding positions could be confirmed without missing by screening the single colonies and analyzing the activities thereof.

Specifically, in order to make a library comprising 20 kinds of amino acids, polymerase chain reaction (PCR) was performed using 100 μl/ml of a pECCG117-CJ1-TNAI_L469P plasmid (Korean Patent Laid-Open Publication No. 10-2010-0016948) as a template and forward and reverse primers. The PCR reaction was performed under the conditions shown in Tables 1 and 2 below. The library obtained by the PCR reaction was transformed into an *E. coli* K12 DH5α strain to make colonies. The plasmid used was expressed in the *E. coli* strain and the activity thereof in the *E. coli* strain was tested, because it could be replicated and expressed in both *E. coli* and Coryne-type bacteria.

Figure 3:
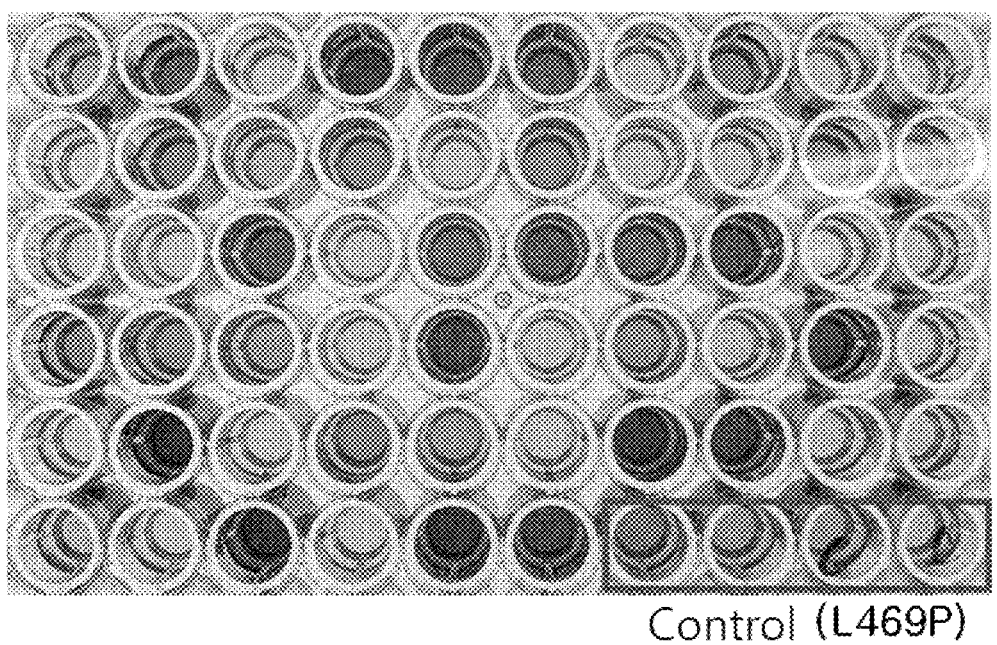
FIG. 3 shows the results obtained by subjecting the residue at 275 of L-arabinose isomerase to saturated mutagenesis and comparing the relative activity of variants, selected by the cysteine-carbazole method, through a color development reaction. A considerable number of variants showing an activity higher than that of a control were found.

The activities of isomerases expressed from 110 colonies obtained as described were analyzed by a cysteine-carbazole method (Dische, Z., and E. Borenfreund., A New Spectrophotometric Method for the Detection and Determination of Keto Sugars and Trioses, J. Biol. Chem., 192:583-587, 1951), and as a result, a number of clones having an activity higher than that of the control (L469P) could be found (FIG. 3).

Among them, 10 colonies measured to have the highest activity were selected and sequenced. As a result, as expected, it could be seen that the activity was higher in the order of valine, methionine and isoleucine (amino acid sequences of SEQ ID NOS: 3 to 5 and nucleotide sequences of SEQ ID NOS: 8 to 10). In addition, mutations in amino acids other than the amino acid at position 275 were not found, suggesting that the phenylalanine residue at position 275 functions to inhibit the reactivity of D-galactose.

Figure 4:
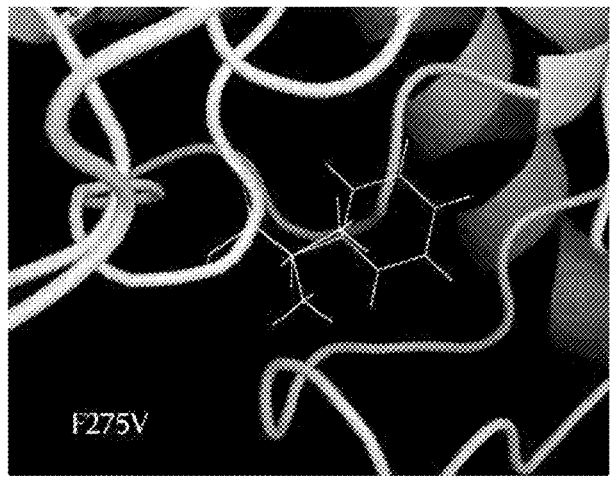
FIG. 4 shows the structures of selected variants (F275V/L469P, F275M/L469P, and F275I/L469P), predicted by a molecular modeling technique.
Figure 4:
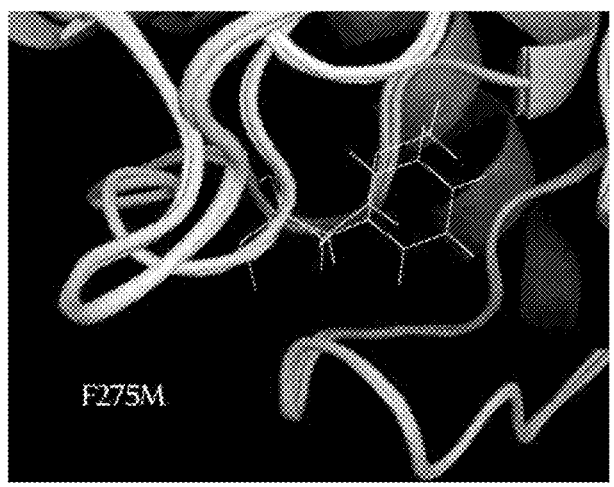
Figure 4:
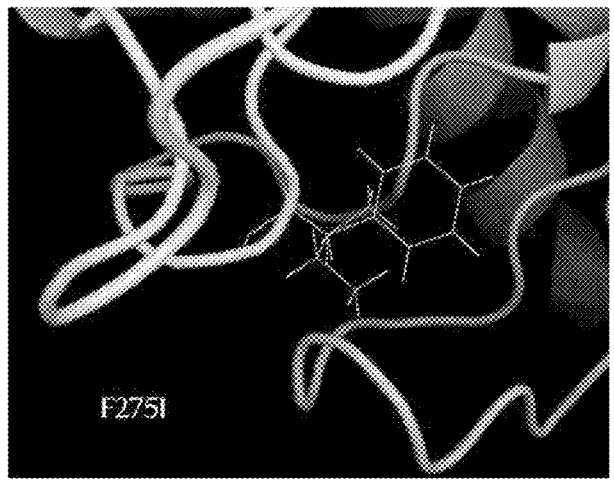

In order to examine whether the mutation has any effect on the isomerase, the structures of the variants were predicted by a molecular modeling technique (FIG. 4). The results of prediction of the structures indicated that the three amino acids all substituted for the phenylalanine at position 275 without causing significant changes in the two- and three-dimensional structures. Thus, it could be anticipated that the reactivity of the isomerase with D-galactose would increase without significant increases in the thermal stability and other production indices.

The variants were transformed into *Corynebacterium glutamicum* ATCC 13032 to produce recombinant strains. The recombinant strains were named "*Corynebacterium glutamicum* pFIS-1-TNAI-2, pFIS-1-TNAI-3 and pFIS-1-TNAI-4", respectively, and were deposited with the Korean Culture Center of Microorganisms (361-221, Honje 1-dong, Seodaemun-gu, Seoul, South Korea), an international depository authority, on Feb. 14, 2013 under the accession numbers KCCM11378P, KCCM11379P and KCCM11380P, respectively.

TABLE 1

| Saturated mutagenesis PCR | |
|---|---|
| Composition of reaction solution | Amount (μl) added |
| PCR buffer (pfu-ultra) 10X | 5 |
| dNTP (2.5 mM) | 5 |
| pCJ1-TNAI_L469P | 1 |
| TNAI275_F primer | 1 |
| TNAI275_R primer | 1 |
| pfu-ultra | 1 |
| DDW | To 50 μl |

TABLE 2

| PCR reaction conditions | | | |
|---|---|---|---|
| Step | Temperature | Time | Cycles |
| Initial denaturation | 95° C. | 5 min | 1 |
| Denaturation | 95° C. | 45 sec | 18 |
| Annealing | 60° C. | 45 sec | |
| Extension | 68° C. | 18 min | |
| Final extension | 72° C. | 10 min | 1 |

Example 3

Expression of Arabinose Isomerase Variants in Microorganisms of the Genus *Corynebacterium*

In order to measure the degree of increases in the activities of the selected variants and the applicability of the variants to the actual production of D-tagatose, the three variants were expressed in microorganisms of the genus *Corynebacterium*, and studies on productivity and production related indices were performed.

The three variants selected in Example 2 were transformed into *Corynebacterium glutamicum* ATCC 13032 to produce recombinant strains. These recombinant strains were cultured in media (20 g/L glucose, 10 g/L poly peptone, 10 g/L yeast extract, 10 g/L ammonium sulfate, 5.2 g/L KH$_2$PO$_4$, 10.7 g/L K$_2$HPO$_4$, 0.5 g/L MgSO$_4$, 1.5 g/L urea, 1.8 mg/L D-biotin, 9 mg/L thiamine, mg/L Ca-panthothenic, 60 mg/L niacinamide) containing 50 μg/ml of kanamycin 30° C. for 20 hours to induce the expression of the recombinant arabinose isomerase mutants.

In order to measure the activity of the expressed arabinose isomerases, the cultures were centrifuged at 8000 g-force for 10 minutes to collect bacterial cells which were then resuspended in 50 mM Tris-HCl (pH 7.5) buffer. The suspended cells were treated with 0.1% POESA at room temperature for 1 hour to weaken the cell wall. Then, centrifugation was performed again under the above-described conditions to collect the cells which were then resuspended in a mixed solution of 300 g/L D-galactose, 5 mM manganese chloride and 50 mM Tris-HCl (pH 7.5) to a concentration of 4% (w/v). The suspension was allowed to react at 75° C. for 1 hour, and HPLC analysis (WATERS HPLC, EMPOWER system, WATERS SugarPak ID 6.5-L 300 mm column, 2414 Refractive Index Detector) was performed for quantification of D-galactose and D-tagatose.

The results of one hour of the reaction indicated that the control L469P produced 35 g/L of D-tagatose, whereas the variant F275V/L469P showed a productivity of 121 g/L·h, the variant F275M/L469P showed a productivity of 117 g/L·h, and the variant F275I/L469P showed 101 g/L·h.

Example 4

Isolation of Arabinose Isomerase Variants Expressed in Coryne Bacteria 200 mL of the recombinant strain comprising each of the three variants (F275V/L469P, F275M/L469P, and TNAI-F275I/L469P) whose activities were confirmed, and the control L469P, was seed-cultured in a 2 L flask under the same conditions as described in Example 3. In order to examine whether the arabinose isomerases were expressed, the activities of the isomerases were measured using a portion of each of the cultures under the same conditions described in Example 3.

Bacterial cells obtained from each of the cultures were resuspended in 20 mM Tris-HCl buffer (pH 7.5) containing 0.1 mM manganese chloride, and were lysed using a high-pressure cell homogenizer T-series (4.0 kW: Constant systems, UK). To remove endogenous proteins other than the isomerases, the cells were heat-treated at 75° C. for 20 minutes. The heat-treated cell debris was removed by centrifugation at 8,000 g-force for 10 minutes, and then the cell debris and lipids were further removed by ultracentrifugation (BECKMAN COULTER Optima L-80 XP Ultracentrifuge) at 60,000 g-force.

The resulting cell extract was purified by anion exchange chromatography (Mono QTM 10/100GL, GE Healthcare). The purified cell extract was pre-equilibrated with a binding solution (50 mM NaCl, 0.1 mM manganese chloride, 20 mM Tris-HCl (pH7.5), and then an excess amount of the cell extract was bound and fractionated while increasing the ratio of an eluent solution [1M NaCl, 0.1 mM manganese chloride, 20 mM Tris-HCl (pH7.5). Fractions showing activity for the substrate D-galactose was selected through a cysteine-carbazole-sulfuric acid method, and then analyzed by SDS-PAGE.

Figure 5:
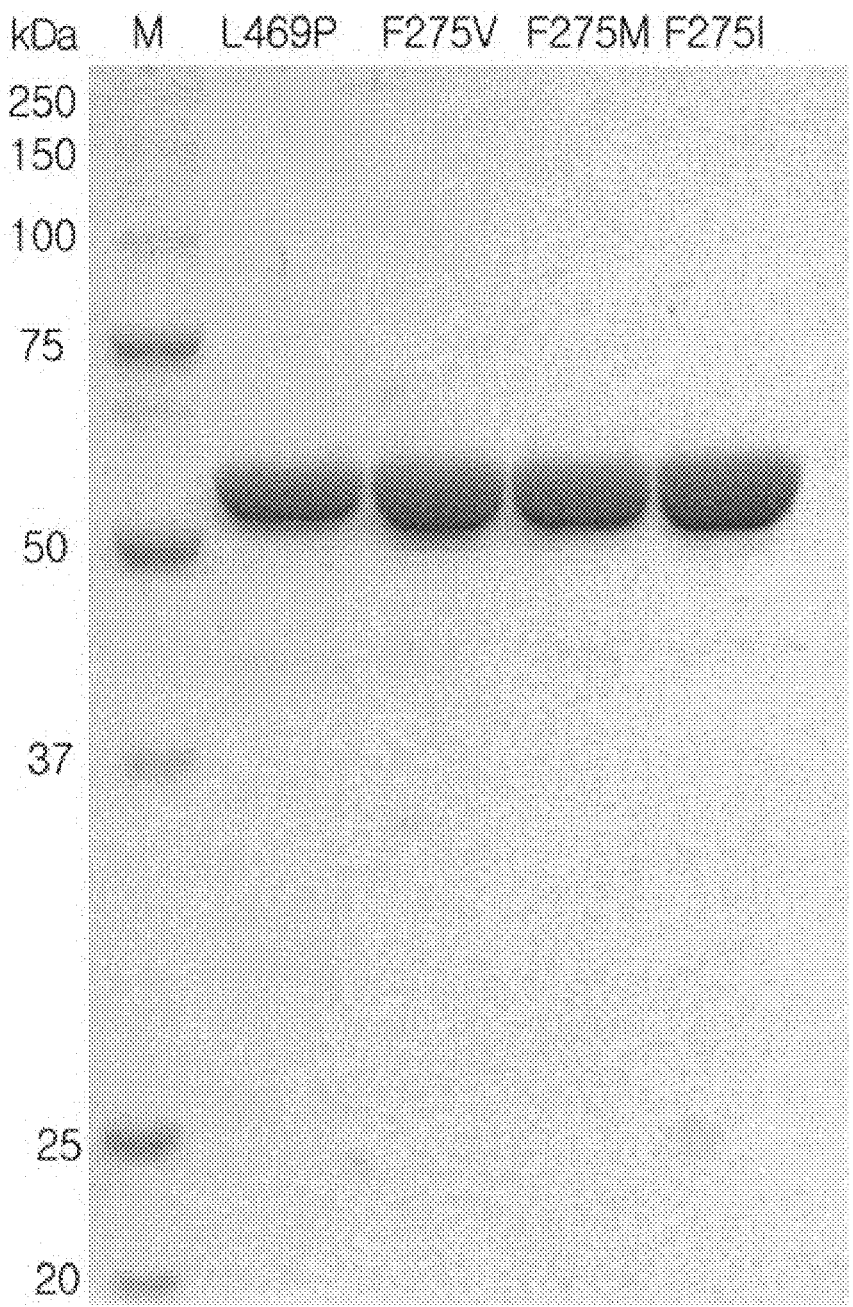
FIG. 5 shows the results of SDS-PAGE analysis of isolated and purified *Thermotoga neapolitana* L-arabinose isomerase variants.

As a result, it could be seen that the purified protein had a molecular weight of about 56 kDa, which is consistent with the known molecular weight of *Thermotoga neapolitana* arabinose isomerase. A fraction having the highest degree of purification was selected by SDS-PAGE, and a high concentration of NaCl was removed therefrom using a PD-10 desalting column (GE Healthcare). The resulting purified enzyme was analyzed by SDS-PAGE (FIG. 5). The isolated and purified protein was quantified using a Bradford assay, and BSA (bovine serum albumin) was used as a standard protein.

Example 5

Studies on Characterization of Arabinose Isomerase Variants

It was found that the three arabinose isomerase variants prepared in the above Example showed significantly increased activities compared to the variant having a substitution of proline for leucine at position 469. Based on this finding, experiments on parameters related on reaction conditions having effects on the actual production of D-tagatose were performed.

5-1: Study on Optimum Temperature

*Thermotoga neapolitana* arabinose isomerase, a thermophilic enzyme, has relatively high thermal stability and the optimum temperature. The temperature suitable for producing D-tagatose from D-galactose is between 55° C. and 75° C. At a temperature lower than 55° C., problems resulting from contamination with heterologous strains will occur, and at a temperature higher than 75° C., problems will arise in terms of the stability of D-tagatose produced. The wild-type arabinose isomerase or the control L469P, the optimum reaction temperature of which is 85° C., had a problem in that it shows relatively low activity at a temperature at which the production process is applicable.

In order to examine the optimum temperatures of the arabinose isomerase variants purified in Example 4, each of the purified enzymes was added to 100 mM D-galactose substrate, and the activity thereof was measured in 50 mM Tris-HCl buffer (pH 7.5) containing 1 mM manganese chloride (MnCl$_2$) at a temperature ranging from 60° C. to 90° C. at intervals of 5° C.

Figure 6:
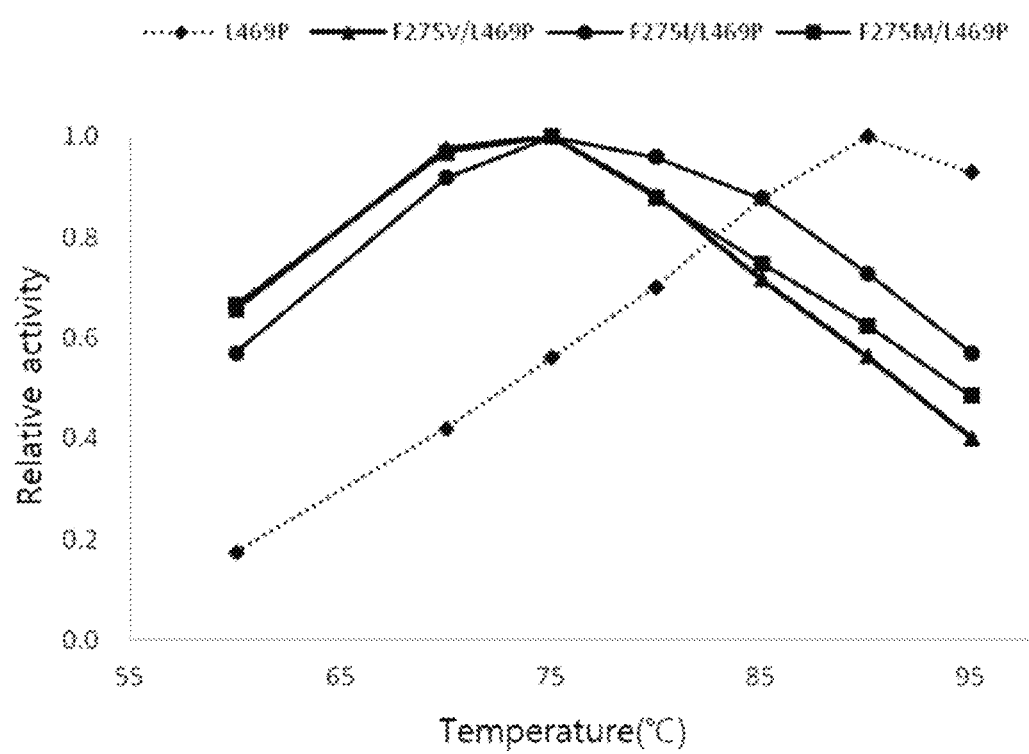
FIG. 6 shows the results of evaluating the relative activity of selected variants at varying temperatures to determine the optimum temperatures of the variants.

The measurement of the activity was performed by a cysteine-carbazole method. As shown in FIG. 6, the results of measuring the enzymatic activity as a function of temperature indicated that the optimum reaction temperature of the three arabinose isomerase variants was 75° C., which was 10° C. lower than that of L469P. Thus, it was found that the activity of the isomerases in the temperature range in which the production process is applicable would be generally high and that the temperature range of application of the production process would be broader.

In addition, the three variants showed similar temperature patterns, suggesting that the characteristics of the phenylalanine residue at position 275 have effects on the optimum reaction temperature. Thus, it can be seen that sufficient flexibility should be ensured so that the steric hindrance of phenylalanine at position 275 with D-galactose during the reaction of the isomerase with D-galactose can be minimized. As the temperature increases, the molecular motion of the phenyl residue of phenylalanine and the surrounding residues can be more active, and thus the steric hindrance with carbon 6 of D-galactose can be reduced. At the same time, it can be anticipated that the optimum temperature can be formed within a range that does not significantly influence the three- and four-dimensional structures of the protein. Thus, there can be a change in the optimum temperature of the variants whose steric hindrance has been essentially reduced by the mutation at position 275. However, additional analysis and experiments are required to scientifically prove this fact.

5-2: Study on Thermal Stability

In order to examine the thermal stability of the arabinose isomerase variants, each of the purified enzymes was added to a solution of 50 mM Tris-HCl (pH 7.5) and 1 mM manganese chloride at a concentration of 20 μg/ml and incubated in a constant-temperature water bath at 95° C. for 180 minutes. An enzymatic reaction was performed using an enzyme solution sampled at varying time points to measure the residual activity of the enzyme.

Figure 7:
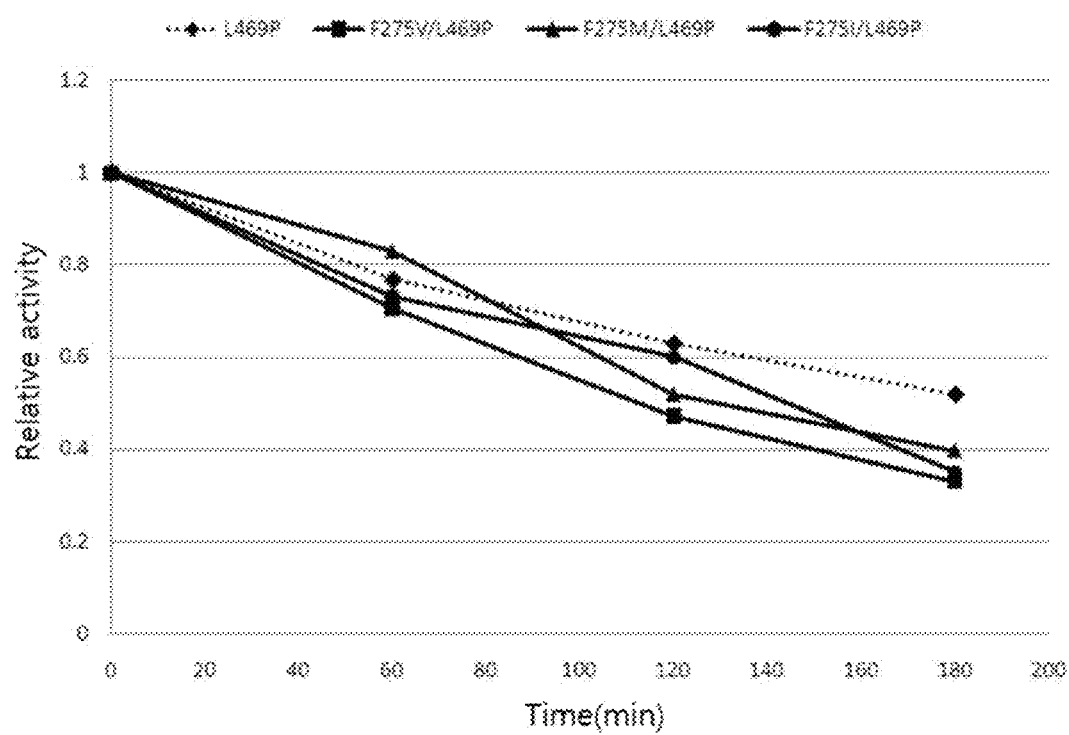
FIG. 7 shows the results of measuring the thermal stabilities of selected variants 95° C. as a function of time.

As shown in FIG. 7, the results of examination of the thermal stability indicated that the arabinose isomerase variants showed a decrease in the residual activity with time at 95° C., but the difference in thermal stability between the variants was not significant. To obtain more quantitative data, the half-life of the active of each variant was measured. As a result, it was found that L469P had a half-life of about 3 hours, and the variants having the mutation at position 275 had a half-life of about 2 hours (Table 3). The thermal stabilities of the variants having the mutation at position 275 were measured to be relatively low, but it is believed that the difference in the thermal stability is not significant and can be sufficiently offset by the increase in the activity and the decrease in the process temperature.

TABLE 3

Half-lives of arabinose isomerases, measured at 95° C.

| Variants | Half-life (minutes) |
|---|---|
| L469P | 185 |
| F275V/L469P | 122 |
| F275M/L469P | 126 |
| F275I/L469P | 134 |

5-3: Study on the Change in Activity Caused by the Effect of Metal Ions

Many enzymes require metal ions for catalysis. For this reason, in order to examine the dependence of the thermal stability of the arabinose isomerase variants of the present invention on metal ions, the change in the activity of the variants by metal ions was examined using each of the purified enzymes.

Figure 8:
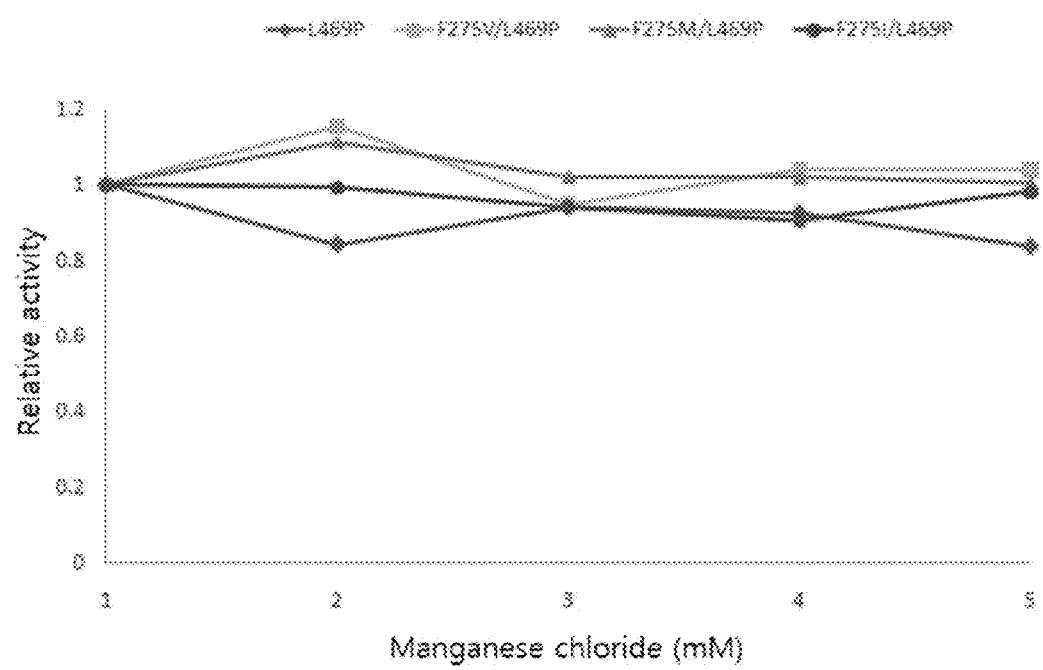
FIG. 8 shows the results of evaluating the relative activity of selected variants to determine the dependence of the variants on manganese.

In order to examine the change in the activity of the enzyme as a function of the concentration of the enzyme, each of the purified enzymes was added to 100 mM D-galactose substrate, and the activity of each enzyme was measured in a 50 mM Tris-HCl (pH 7.5) buffer solution containing 1-5 mM of manganese chloride ($MnCl_2$) at 75° C. for 10 minutes (FIG. 8). As a result, it could be seen that all the variants showed similar activities within the manganese chloride concentration range used in the experiment and that the effect of manganese ions on the activity of the isomerases at the manganese chloride concentration essential for the activity of the enzyme was not significant.

5-4: Study on Activity of Enzymes

In order to examine the reaction rates of the enzymes, the specific activities of the arabinose isomerase variants were measured at a reaction temperature of 75° C. Specifically, each of the enzymes was added to 1 mM manganese chloride and 100 mM D-galactose, and the reactivity of 1 mg of the enzyme was measured at pH 7.5 and 75° C. The specific activity of each enzyme during the reaction was measured under the above conditions for 10 minutes, and as a result, it was shown that the specific activities of the variants having the mutation at position 275 were about 5.5 times (F275V), 5 times (F275M) and 3.9 times (F275I), respectively, higher than that of L469P (Table 4).

TABLE 4

| Specific activities of variants | | | | |
|---|---|---|---|---|
| | L469P | F275V/L469P | F275M/L469P | F275I/L469P |
| Specific activity (U/mg) | 2.4 | 13.1 | 12.1 | 9.3 |

Accession Numbers

Depository authority: Korean Culture Center of Microorganisms;
Accession number: KCCM11378P;
Deposit date: Feb. 14, 2013.
Depository authority: Korean Culture Center of Microorganisms;
Accession number: KCCM11379P;
Deposit date: Feb. 14, 2013.
Depository authority: Korean Culture Center of Microorganisms;
Accession number: KCCM11380P;
Deposit date: Feb. 14, 2013.

The invention claimed is:

1. An arabinose isomerase variant having an increased activity of converting D-galactose into D-tagatose, the arabinose isomerase variant having a substitution of an amino acid other than phenylalanine for an amino acid at position 275 and a substitution of proline for an amino acid at position 469 of the amino acid sequence set forth in SEQ ID NO: 1.

2. The arabinose isomerase variant of claim 1, wherein the substitution of the amino acid for the amino acid at position 275 is any one amino acid selected from the group consisting of valine, methionine and isoleucine.

3. A polynucleotide encoding the arabinose isomerase variant of claim 1.

4. The polynucleotide of claim 3, which has a nucleotide sequence of SEQ ID NO: 8, SEQ ID NO: 9 or SEQ ID NO: 10.

5. A microorganism of the genus *Corynebacterium* transformed with a recombinant vector comprising the polynucleotide of claim 3.

6. The microorganism of claim 5, which is *Corynebacterium glutamicum*.

7. The microorganism of claim 5, which is *Corynebacterium glutamicum* pFIS-1-TNAI-2 (KCCM 11378P), pFIS-1-TNAI-3 (KCCM 11379P) or pFIS-1-TNAI-4 (KCCM 11380P).

8. A method for producing D-tagatose, the method comprising culturing the microorganism of claim 5.

9. The method of claim 8, which comprises reacting a solution containing D-galactose with a metal ion source selected from the group consisting of manganese chloride, magnesium chloride and zinc chloride in the presence of the microorganism.

10. The method of claim 9, wherein the manganese chloride is added at a concentration of 0.1 to 10 mM.

11. A method for producing D-tagatose, the method comprising culturing the microorganism of claim 6.

12. The method of claim 11, which comprises reacting a solution containing D-galactose with a metal ion source selected from the group consisting of manganese chloride, magnesium chloride and zinc chloride in the presence of the microorganism.

13. The method of claim 12, wherein the manganese chloride is added at a concentration of 0.1 to 10 mM.

14. A method for producing D-tagatose, the method comprising culturing the microorganism of claim 7.

15. The method of claim 14, which comprises reacting a solution containing D-galactose with a metal ion source selected from the group consisting of manganese chloride, magnesium chloride and zinc chloride in the presence of the microorganism.

16. The method of claim 15, wherein the manganese chloride is added at a concentration of 0.1 to 10 mM.

* * * * *